(12) United States Patent
Magwire et al.

(10) Patent No.: US 12,369,542 B2
(45) Date of Patent: Jul. 29, 2025

(54) GENETIC REGIONS AND GENES ASSOCIATED WITH INCREASED YIELD IN PLANTS

(71) Applicant: SYNGENTA CROP PROTECTION AG, Basel (CH)

(72) Inventors: Michael Mahlon Magwire, Research Triangle Park, NC (US); Robert John Bensen, Osage, MN (US); Allison Weber, Willdwood, MO (US); Satya Chintamanani, Slater, IA (US); Elhan Sultan Ersoz, Champaign, IL (US); Yuejin Sun, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 539 days.

(21) Appl. No.: 17/268,530

(22) PCT Filed: Sep. 4, 2019

(86) PCT No.: PCT/US2019/049414
§ 371 (c)(1),
(2) Date: Feb. 15, 2021

(87) PCT Pub. No.: WO2020/051166
PCT Pub. Date: Mar. 12, 2020

(65) Prior Publication Data
US 2021/0307276 A1    Oct. 7, 2021

Related U.S. Application Data

(60) Provisional application No. 62/728,121, filed on Sep. 7, 2018.

(51) Int. Cl.
| | | |
|---|---|---|
| *A01H 6/46* | (2018.01) | |
| *A01H 1/00* | (2006.01) | |
| *A01H 1/04* | (2006.01) | |
| *C12Q 1/68* | (2018.01) | |
| *C12Q 1/6895* | (2018.01) | |

(52) U.S. Cl.
CPC ........... *A01H 1/1225* (2021.01); *A01H 1/045* (2021.01); *A01H 6/4684* (2018.05); *C12Q 1/6895* (2013.01); *C12Q 2600/13* (2013.01)

(58) Field of Classification Search
None
See application file for complete search history.

(56) References Cited

U.S. PATENT DOCUMENTS

2006/0141495 A1 *   6/2006   Wu .................. C12Q 1/6895
                                                 800/320.1

FOREIGN PATENT DOCUMENTS

WO    2017/106274 A1    6/2017

OTHER PUBLICATIONS

International Search Report for International Application No. PCT/US2019/049414 mailed Jan. 9, 2020.
GenBank Accession No. AC205313.4, Zea mays cultivar B73 chromosome 1 clone ZMMBBb-243M6, *Sequencing in Process*, 9 unordered pieces, Sep. 23, 2013 [online]. [Retrieved on Nov. 9, 2019]. Retrieved from the internet: <URL: https://www.ncbi.nim.nih.gov/nuccore/AC205313>, Entire document.
GenBank Accession No. BT017742.1, Zea mays clone EL01N0449E04.c mRNA sequence, 21, Dec. 2007 [online]. [Retrieved on Nov. 9, 2019]. Retrieved from the internet: <URL: https://www.ncbi.nim.nih.gov/nuccore/BT017742>, Entire document.
Breton Ghislain et al: "Expression Profiling & Bioinformatic Analyses of a Novel Stress-Regulated Multispanning Transmembrane Protein Family from Cereals & Arabidopsis"; Plant Physiology, vol. 132(1); May 1, 2003, pp. 64-74 (XP055921163); USA, ISSN: 0032-0889; DOI: 10.1104, p. 102.015255; Retrieved from the Internet: URL: http://academic.oup.com/plphsys/article-pdf/132/1/64/38698843/plphys_v132_1_64.pdf.
Woldesemayat Adugna Abdi et al: "Cross-species multiple environmental stress responses: An integrated approach to identify candidate genes for multiple stress tolerance in sorghum (Sorghum bicolor (L.) Moench) & related model species", PLoS One; Jan. 1, 2018, pp. e0192678-e0192678 (XP055921157) USA, DOI: 10.1372/journal.pone.0192678 (retrieved on May 13, 2022).
Supplementary Partial European Search Report mailed May 30, 2022 in EP Application No. 19856993.1.
Chunhui Li et al: "Numerous genetic loci identified for drought tolerance in the maize nested association mapping populations": BMC Genomics, Biomed Central Ltd., London, UK; vol. 17(1), Nov. 8, 2016, pp. 1-11 (XP021238031).

* cited by examiner

*Primary Examiner* — Medina A Ibrahim
(74) *Attorney, Agent, or Firm* — Dale Skalla

(57) ABSTRACT

The present invention relates to methods and compositions for identifying, selecting and/or producing a plant or germplasm having root increased drought tolerance and/or increased yield under non-drought conditions as compared to a control plant. A maize plant, part thereof and/or germplasm, including any progeny and/or seeds derived from a maize plant or germplasm identified, selected and/or produced by any of the methods of the present invention is also provided.

17 Claims, No Drawings
Specification includes a Sequence Listing.

GENETIC REGIONS AND GENES ASSOCIATED WITH INCREASED YIELD IN PLANTS

CROSS-REFERENCE TO RELATED APPLICATIONS

This application is a 371 of International Application No. PCT/US2019/049414 filed Sep. 4, 2019, which claims priority to U.S. Application No. 62/728,121, filed Sep. 7, 2018, the contents of which are incorporated by reference herein.

STATEMENT REGARDING ELECTRONIC SUBMISSION OF A SEQUENCE LISTING

A Sequence Listing in ASCII text format, submitted under 37 C.F.R. § 1.821, entitled "81647_ST25", 69 kilobytes is attached and filed herewith and is incorporated herein by reference.

FIELD OF THE INVENTION

The present invention relates to compositions and methods for introducing into a plant alleles, genes and/or chromosomal intervals that confer in said plant the traits of increased drought tolerance and/or increased yield under water stressed conditions and/or increased yield in the absence of water stress.

BACKGROUND

Drought is one of the major limitations to maize production worldwide. Around 15% of the world's maize crop is lost every year due to drought. Periods of drought stress can occur at any time during the growing season. Maize is particularly sensitive to drought stress in the period just before and during flowering. When drought stress occurs during this critical period, a significant decrease in grain yield can result.

Identifying genes that enhance the drought tolerance of crops could lead to more efficient crop production practices by allowing for the identification, selection and production of crop plants with increased drought tolerance.

As such, a goal of plant breeding is to combine, in a single plant, various desirable traits. For field crops such as corn, soybean, etc. these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Once discovered, these desirable loci can be selected for as part of a breeding program in order to generate plants that carry desirable traits. An exemplary embodiment of a method for generating such plants includes the transfer by introgression of nucleic acid sequences from plants that have desirable genetic information into plants that do not by crossing the plants using traditional breeding techniques. Further, one may use newly invented genome editing capabilities to edit a plant genome to comprise desirable genes or genetic allelic forms.

Desirable loci can be introduced into commercially available plant varieties using marker-assisted selection (MAS), marker-assisted breeding (MAB), transgenic expression of gene(s) and/or through recent gene editing technologies such as, for example CRISPR, TALEN, etc.

What are needed, then, are new methods and compositions for introducing into a plant a gene or genomic region that may result in drought tolerant crops and/or crops that have increased yield in both well-watered and water stressed conditions.

SUMMARY OF THE INVENTION

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

Compositions and methods for identifying, selecting and/or producing plants with increased yield under drought conditions are provided. As described herein, a genomic regions (interchangeably-"chromosome intervals") may comprise, consist essentially of or consist of gene(s), a single allele or a combination of alleles at one or more genetic loci associated with increased drought tolerance and/or increased yield.

All disclosed maize chromosome positions herein correspond with the maize "B73 reference genome version 2". The "B73 reference genome, version 2" and "B73 reference genome, version 4" are publically available physical and genetic frameworks of the maize B73 genome. They are the result of a sequencing effort utilizing a minimal tiling path of approximately 19,000 mapped BAC clones, and focusing on producing high-quality sequence coverage of all identifiable gene-containing regions of the maize genome. These regions were ordered, oriented, and along with all of the intergenic sequences, anchored to the extant physical and genetic maps of the maize genome. They can be accessed using a genome browser, the Maize Genome Browser that is publicly available on the internet that facilitates user interaction with sequence and map data at the Maize Genetic and Genomics Database, maizeGDB.org, Portwood J L II et al. MaizeGDB 2018: the maize multi-genome genetics and genomics database. Nucleic Acids Res. 2018.

The present invention has identified twelve causative chromosome interval, QTL, genes and/and alleles (collectively herein 'loci') within the maize genome that are highly associated with increased drought tolerance (e.g. increased bushels of corn per acre under drought conditions) and with increased yield (e.g. increased bushels of corn per acre under normal or well-watered conditions), these twelve loci collectively referred to herein as ('yield alleles' or 'yield QTL" interchangeably). Specifically, the invention discloses the following twelve yield QTL including:

(1) QTL 1 (herein, ('QTL 1')) located on maize chromosome 1 corresponding to GRMZM 2G040030 and comprising an A allele at position 280976157;

(2) QTL 2 (herein, ('QTL 2')) located on maize chromosome 1 corresponding to GRMZM2G040030 and comprising a G allele at position 280976564;

(3) QTL 3 (herein, ('QTL 3')) located on maize chromosome 1 corresponding to GRMZM2G843914 and comprising a C allele at position 281072679;

(4) QTL 4 (herein, ('QTL 4')) located on maize chromosome 2 corresponding to GRMZM2G160994 and comprising an A allele at position 44262624;
(5) QTL 5 (herein, ('QTL 5')) located on maize chromosome 9 corresponding to GRMZMG020721 and comprising a C allele at position 134300637;
(6) QTL 6 (herein, ('QTL 6')) located on maize chromosome 9 corresponding to GRMZMG080501 and comprising an A allele at position 135348128;
(7) QTL 7 (herein, ('QTL 7')) located on maize chromosome 9 corresponding to GRMZM2G080501 and comprising an G allele at position 135348898;
(8) QTL 8 (herein, ('QTL 8')) located on maize chromosome 9 corresponding to GRMZM2G049322 and comprising an C allele at position 138889589;
(9) QTL 9 (herein, ('QTL 9')) located on maize chromosome 9 corresponding to GRMZM2G049322 and comprising an C allele at position 138889629;
(10) QTL 10 (herein, ('QTL 10')) located on maize chromosome 9 corresponding to GRMZM2G049322 and comprising an G allele at position 138889963;
(11) QTL 11 (herein, ('QTL 11')) located on maize chromosome 9 corresponding to GRMZM2G049322 and comprising an G allele at positions 138890220; and
(12) QTL 12 (herein, ('QTL 12')) located on maize chromosome 5 corresponding to GRMZM2G108716 and comprising a G allele at position 2795884.

Not to be limited by theory, it is believed that each of these yield alleles fall within a gene(s) that are causative for the given phenotype of drought tolerance and/or increased yield. It is well known in the art that markers within the causative gene and all closely associated markers may be used in marker assisted breeding to select for, identify and assist in producing plants having the trait associated with the given marker (e.g. in this case, increased drought tolerance and/or yield, See Table 1 demonstrating list of probable causative genes, alleles and examples of closely associated markers that may be used to identify or produce maize lines having increased drought tolerance). Accordingly, in one aspect of the invention is disclosed a method of selecting or identifying a maize line or germplasm having increased drought tolerance and or yield wherein the method comprises the steps of; (a) isolating a nucleic acid from a maize plant part; (b) detecting in the nucleic acid of (a) a molecular marker that is associated with drought tolerance and/or increased yield wherein the molecular marker is closely associated with any one of "Yield QTL 1-12" wherein closely associated means the marker is within 50 cM, 40 cM, 30 cM, 20 cM, 15 cM, 10 cM, 9 CM, 8 CM, 7 CM, 6 CM, 5 CM, 4 cM, 3 cM, 2 cM, 1 cM or 0.5 cM of the said Yield QTL; and (c) selecting or identifying a maize plant on the basis of the presence of said marker in (b). In some embodiments the marker of (b) can be used to produce maize plants having increased drought tolerance and or increased yield by selecting a maize plant according to the method described in steps (a)-(c) above and further comprise the steps of (d) crossing the plant of (c) with a second maize plant not comprising the marker identified in (b); and (d) producing a progeny plant comprising in its genome the marker of (b) wherein said progeny plant has increased drought tolerance and/or yield as compared to a control plant.

In some embodiments of the present invention, a method of identifying and/or selecting a drought tolerant maize plant, germplasm or part thereof is provided, the method comprising: detecting, in said maize plant or part thereof, at least one allele of a marker locus that is associated with drought tolerance in maize, wherein said one or more marker locus is located within a chromosomal interval within 50 cM, 40 cM, 30 cM, 20 cM, 15 cM, 10 cM, 9 cM, 8 cM, 7 cM, 6 CM, 5 CM, 4 cM, 3 cM, 2 cM, 1 cM or 0.5 cM of the said Yield QTL.

In some embodiments, methods of producing a drought tolerant maize plant are provided. Such methods can comprise detecting, in a maize germplasm or plant, the presence of a marker associated with increased drought tolerance (e.g. a marker within any chromosomal interval or combination thereof comprising at least one QTL 1-12 as herein defined) and producing a progeny plant from said maize germplasm or plant wherein said progeny plant comprises said marker associated with increased drought tolerance and said progeny plant further demonstrates increased drought tolerance as compared to a control plant not comprising said marker. The invention also provides seed produced from said progeny plant.

In some embodiments, Yield QTL 1 comprises an A at position 500 of SEQ ID NO: 1, QTL 2 comprises a G at position 500 of SEQ ID NO:2, QTL 3 comprises a C at position 501 of SEQ ID NO:3, QTL 4 comprises an A at position 501 of SEQ ID NO:4, QTL 5 comprises a C at position 502 of SEQ ID NO:5, QTL 6 comprises an A at position 501 of SEQ ID NO:6, QTL 7 comprises a G at position 501 of SEQ ID NO:7, QTL 8 comprises a C at position 501 of SEQ ID NO:8, QTL 9 comprises an A at position 501 of SEQ ID NO:9, QTL 10 comprises a G at position 501 of SEQ ID NO:10, QTL 11 comprises a G at position 500 of SEQ ID NO:11, and QTL 12 comprises a C at position 448 of SEQ ID NO:12.

In some embodiments, Maize plants comprising Yield QTL 1 can be identified with molecular assay SM6492, Yield QTL 2 can be identified with molecular assay SM6487, Yield QTL 3 can be identified with molecular assay SM5343, Yield QTL 4 can be identified with molecular assay SM5347, Yield QTL 5 can be identified with molecular assay SM6647, Yield QTL 6 can be identified with molecular assay SM6652, Yield QTL 7 can be identified with molecular assay SM6646, Yield QTL 8 can be identified with molecular assay SM5575, Yield QTL 9 can be identified with molecular assay SM5572, Yield QTL 10 can be identified with molecular assay SM5570, Yield QTL 11 can be identified with molecular assay SM5584, and Yield QTL 12 can be identified with molecular assay SM6552

In some embodiments, the presence of a marker associated with increased drought tolerance is detected using a marker probe. In some such embodiments, the presence of a marker associated with increased drought tolerance is detected in an amplification product from a nucleic acid sample isolated from a maize plant or germplasm. In some embodiments, the marker comprises a haplotype, and a plurality of probes are used to detect the alleles that make up the haplotype. In some such embodiments, the alleles that make up the haplotype are detected in a plurality of amplification products from a nucleic acid sample isolated from a maize plant or germplasm.

In some embodiments, methods of selecting a drought tolerant maize plant or germplasm are provided. Such methods can comprise crossing a first maize plant or germplasm with a second maize plant or germplasm, wherein the first maize plant or germplasm comprises a marker associated with increased drought tolerance, and selecting a progeny plant or germplasm that possesses the marker (e.g. a marker located 50 cM, 20 cM, 10 cM, 5 CM, 2 cM or 1 cM from any one of QTL 1-12, that have been demonstrated to associate with increased drought tolerance and/or yield.

In some embodiments, methods of introgressing an allele associated with increased drought tolerance into a maize plant or germplasm are provided. Such methods can comprise crossing a first maize plant or germplasm comprising an allele associated with increased drought tolerance (e.g. any allele as identified in QTL 1-12 or closely associated alleles thereof) with a second maize plant or germplasm that lacks said allele and repeatedly backcrossing progeny plants comprising said allele with the second maize plant or germplasm to produce a drought tolerant maize plant or germplasm comprising the allele associated with increased drought tolerance. Progeny comprising the allele associated with increased drought tolerance can be identified by detecting, in their genomes, the presence of a marker associated with said allele; for example a marker located within a chromosomal interval (e.g. any of QTLs 1-12 or a portion thereof or within 50 cM, 20 cM, 10 cM or less from QTLs 1-12 or any combination thereof.

Plants and/or germplasms identified, produced or selected by any of the methods of the invention are also provided, as are any progeny or seeds derived from a plant or germplasm identified, produced or selected by these methods.

Non-naturally occurring maize plants and/or germplasms having introgressed (e.g. through plant breeding, transgenic expression or genome editing) into its genome any one of yield alleles 1-12 associated with increased drought tolerance are also provided. In some embodiments the non-naturally occurring maize plant and/or germplasm is a progeny plant of a maize plant that has been selected for breeding purposes on the basis of the presence of a marker that associates with increased drought tolerance and/or increased yield under well watered conditions and wherein said marker is located within a chromosomal interval that corresponds to any one or more of chromosome interval 1, 2, 3, 4, 5, 6, 7 or portions thereof. In other embodiments, a non-naturally occurring plant is created by editing within a plant's genome an allelic change corresponding to any one of yield alleles 1-12 wherein the allelic change results in a plant having increased drought and/or increase yield as compared to a control plant. In another embodiment, a plant having increased drought tolerance and/or increased yield can be created by modulating the expression of any one of: hey. It is contemplated that one could modulate said expression via modification of native corn regulatory elements (e.g. native promoter upstream from respective gene)

Methods of employing markers associated with increased drought tolerance are also provided. Such markers can comprise a nucleotide sequence at least 85%, 90%, 95%, or 99% identical to any of QTLs 1-12 or the reverse complement thereof, or an informative or functional fragment thereof.

Compositions comprising a primer pair capable of amplifying a nucleic acid sample isolated from a maize plant or germplasm to generate a marker associated with increased drought tolerance are also provided. In one embodiment the amplifying of the primer pair produces an amplicon diagnostic for the presence of any one of QTL 1-12.

A marker associated with increased drought tolerance can comprise, consist essentially of, and/or consist of a single allele or a combination of alleles at one or more genetic loci (e.g. a genetic loci comprising any one of QTLs 1-12 as defined herein).

In another embodiment, the genes, chromosomal intervals, markers and genetic loci of the invention may be combined with the markers described in U.S. Patent Applications 2011-0191892 and/or PCT/US2016/066543, herein both incorporated in their entirety by reference.

In another embodiment, the presently disclosed subject matter discloses a method to produce a plant having increased drought tolerance as compared to a control plant, the method comprising the steps of a) in a plant cell or in vitro, editing a plant's genome (i.e. through CRISPR or TALEN) to comprise a molecular marker (e.g. SNP) associated with increased drought tolerance wherein the molecular marker is any marker as described in yield QTLs 1-12 and further wherein the plant genome did not have said molecular marker previously; b) producing a plant or plant callus from the plant cell of a). In particular the editing comprises any one of yield QTL 1-12 or closely associated alleles thereof.

In some embodiments, "increased water optimization" confers increased or stabilized yield in a water stressed environment as compared to a control plant. Maize plants having enhance water optimization may be selected, identified or produced using any of QTLs 1-12. In some embodiments, the hybrid with increased water optimization can be planted at a higher crop density. In some embodiments, the hybrid with increased water optimization confers no yield drag when under favorable moisture levels. In yet another embodiment the plants comprising any of QTLs 1-12 confer any one of increased drought tolerance or increased yield as compared to a control plant wherein yield is increased bushels of corn per acre or further increased yield (i.e. increased bushels per acre) under non-drought or well-watered conditions.

The presently disclosed subject matter also provides in some embodiments hybrid Zea mays plants produced by the presently disclosed methods, or a cell, tissue culture, seed, or part thereof.

The presently disclosed subject matter also provides in some embodiments inbred Zea mays plants produced by backcrossing and/or selfing and/or producing double haploids from the hybrid Zea mays plants disclosed herein, or a cell, tissue culture, seed, or part thereof.

The presently disclosed subject matter also provides in some embodiments hybrid or inbred Zea mays plants that have been modified to include a transgene. In some embodiments, the transgene encodes a gene product that provides resistance to a herbicide selected from among glyphosate, Sulfonylurea, imidazolinione, dicamba, glufisinate, phenoxy proprionic acid, cycloshexome, traizine, benzonitrile, and broxynil. For example, any hybrid or inbred Zea mays plant having comprised in its genome a transgene encoding any one of glyphosate, Sulfonylurea, imidazolinione, dicamba, glufisinate, phenoxy proprionic acid, cycloshexome, traizine, benzonitrile, and broxynil resistance transgene and further wherein said plant has introgressed into its genome any one of SEQ ID Nos 1-12.

The presently disclosed subject matter also provides in some embodiments Zea mays plants produced by introgressing an allele of interest of a locus associated with increased drought tolerance into a Zea mays germplasm. In some embodiments, the introgressing comprises (a) selecting a Zea mays plant that comprises an allele of interest of a locus associated with increased drought tolerance (i.e. any of QTL 1-12); and (b) introgressing the allele of interest into Zea mays germplasm that lacks the allele.

In another embodiment, the invention provides maize germplasm that has been enriched with any one of QTLs 1-12, wherein enrichment comprises the steps of identifying or selecting lines having the said QTL or yield alleles and crossing these lines with lines not having said intervals or portions thereof and backcrossing to create inbred lines with said intervals or yield alleles then employing said inbred lines into a plant breeding system to create a commercial maize population enriched for said interval or yield alleles thereof (e.g. a commercial hybrid maize population having greater than 30%, 40% or over 50% of its hybrids enriched with said interval or yield alleles as compared to a 5 year historical pedigree of said hybrid maize population having <30% enrichment of said interval or yield alleles.

In further embodiments, a method of identifying and/or selecting a maize plant or plant part having increased yield under non-drought conditions, increased yield stability under drought conditions, and/or increased drought tolerance, comprising: detecting, in a maize plant or plant part, an allele of at least one marker locus that is associated with increased yield under non-drought conditions, increased yield stability under drought conditions, and/or increased drought tolerance in a plant, wherein said at least one marker is selected from the group or a marker located within 50 cM, 40 cM, 30 cM, 20 cM, 15 cM, 10 cM, 9 cM, 8 CM, 7 cM, 6 CM, 5 CM, 4 cM, 3 cM, 2 cM, 1 cM or 0.5 cM of the following causative alleles:

Chromosome 1 comprising an A allele at position 280976157;
Chromosome 1 comprising a G allele at position 280976564;
Chromosome 1 comprising a C allele at position 281072679;
Chromosome 2 comprising an A allele at position 44262624;
Chromosome 9 comprising a C allele at position 134300637;
Chromosome 9 comprising an A allele at position 135348128;
Chromosome 9 comprising a G allele at position 135348898;
Chromosome 9 comprising a C allele at position 138889589;
Chromosome 9 comprising a C allele at position 138889629;
Chromosome 9 comprising a G allele at position 138889963;
Chromosome 9 comprising an G allele at position 138890220; and
Chromosome 5 comprising a G allele at position 2795884; or any combination thereof.

In another embodiment, the invention provides methods of introducing into a plant genome a gene that confers increased drought tolerance or increased yield in said plant. It is contemplated that genes may be introduced via conventional plant breeding methods, transgenic expression, mutation such as by Ethyl methanesulfonate (ESM), or through gene editing such as TALEN, CRISPR, meganuclease, or etc. In some embodiments, not to be limited by theory, a nucleotide sequence comprising any one or more of the gene models listed in Table 1 below may be introduced into a plant's genome to create plants having increased yield and/or increased drought tolerance as compared to a control plant.

TABLE 1

Summary of putative gene models causative for increased drought tolerance and/or increased yield in plants:

| Gene Model | Gene Direction (+ upregulation; - = downregulation) | VS Gene Id | Putative Structure/Function | GO Terms | Other Information |
|---|---|---|---|---|---|
| GRMZM2G040030 | + | Zm00001d034188 | Cold-regulated 413 plasma membrane protein 2 | GO:0016020 membrane; GO:0016021 integral component of membrane | Meta-QTL covering region (GIN, MTA Store) |
| GRMZM2G040030 | + | Zm00001d034188 | Cold-regulated 413 plasma membrane protein 2 | GO:0016020 membrane; GO:0016021 integral component of membrane | Meta-QTL covering region (GIN, MTA Store) |
| GRMZM5G843914 | − | Zm00001d034191 | Electron transporter | | |
| GRMZM2G160994 | − | Zm00001d003500 | Pentacopeptide repeat containing protein mitochondrial | GO:0005515 protein binding | |
| GRMZM2G020721 | + | Zm00001d047600 | Protein REDUCED WALL ACETYLATION 2 | GO:0016020 membrane; GO:0016021 integral component of membrane | Meta-QTL covering region (GIN, MTA Store) |
| GRMZM2G080501 | + | Zm00001d047640 | thiaminase3 | GO:0016787 hydrolase activity; GO:0009228 thiamine diphosphate biosynthetic process; GO:0050334 thiaminase activity | Gene is involved in preventing damage to vitamin B1 and conserving breakdown products (GIN). B1 breakdown and deficiency has been implicated in drought (Hanson et al., 2016). Nearby ASI meta QTL in Iodents (Nicolas) |
| GRMZM2G080501 | + | Zm00001d047640 | thiaminase3 | GO:0016787 hydrolase activity; GO:0009228 thiamine biosynthetic process; GO:0009229 thiamine diphosphate biosynthetic process; GO:0050334 thiaminase activity | Gene is involved in preventing damage to vitamin B1 and conserving breakdown products (GIN). B1 breakdown and deficiency has been implicated in drought (Hanson et al., 2016). Nearby ASI meta QTL in Iodents (Nicolas) |

TABLE 1-continued

Summary of putative gene models causative for increased drought tolerance and/or increased yield in plants:

| Gene Model | Gene Direction (+ upregulation; − = downregulation | VS Gene Id | Putative Structure/Function | GO Terms | Other Information |
|---|---|---|---|---|---|
| GRMZM2G049322 | − | Zm00001d047776 | Phosphatidylinositol N-acetyglucosaminlytransferase subunit P-related | GO:0016740 transferase activity | |
| GRMZM2G049322 | − | Zm00001d047776 | Phosphatidylinositol N-acetyglucosaminlytransferase subunit P-related | GO:0016740 transferase activity | |
| GRMZM2G049322 | − | Zm00001d047776 | Phosphatidylinositol N-acetyglucosaminlytransferase subunit P-related | GO:0016740 transferase activity | |
| GRMZM2G049322 | − | Zm00001d047776 | Phosphatidylinositol N-acetyglucosaminlytransferase subunit P-related | GO:0016740 transferase activity | |
| GRMZM2G108716 | + | Zm00001d012993 | IWS1/SPN1-transcription factor IIS protein | GO:0046872 metal ion binding; GO:0003676 nucleic acid binding; GO:0006351 transcription DNA-templated; GO:0008270 zinc ion binding; GO:0006414 translational elongation; GO:0006355 regulation of transcription, DNA templated; GO:0003746 translation elongation factor activity; GO:0005634 nucleus | Putative gene involved in NUE |

In another aspect of the invention transgenic plants having increased tolerance to drought and/or increased yield may be produced by operably linking any one of the genes in Table 1 or homologs/orthologs thereof to a plant promoter and expressing said gene in plant. For example, it is contemplated that said genes may be expressed either by constitutive or by tissue specific/preferred expression. Not to be limited by example, but it is contemplated that one could target expression to, for example, the corn ear, the shank, reproductive tissue, fruit, seed, or other plant parts to produce transgenic plants having increased yield and/or drought tolerance.

In certain embodiments, alleles of the invention may be employed for either stiff stalk or non-stiff stalk maize.

These and other aspects of the invention are set forth in more detail in the description of the invention below.

BRIEF DESCRIPTION OF THE SEQUENCES

The instant disclosure includes a plurality of nucleotide and/or amino acid sequences. Throughout the disclosure and the accompanying sequence listing, the WIPO Standard ST.25 (1998; hereinafter the "ST.25 Standard") is employed to identify nucleotides. This nucleotide identification standard is summarized below:

| Nucleotide Naming Conventions in WIPO Standard ST.25 | | | |
|---|---|---|---|
| Symbol | Meaning | Symbol | Meaning |
| a | a | k | g or t/u |
| c | c | s | g or c |
| g | g | w | a or t/u |
| t | t | b | g or c or t/u |
| u | u | d | a or g or t/u |
| r | g or a | h | a or c or t/u |
| v | t/u or c | v | a or g or c |
| m | a or c | n | a or g or c or t/u, unknown, other, or absent |

Additionally, whether specifically noted or not, for each recitation of "n" in the Sequence Listing, it is understood that any individual "n" (including some or all n's in a sequence of consecutive n's) can represent a, c, g, t/u, unknown, or other, or can be absent. Thus, unless specifically defined to the contrary in the Sequence Listing, an "n" can in some embodiments represent no nucleotide.

SEQ ID NO: 1 SM6492 is a subsequence of QTL 1 located on maize chromosome 1 corresponding to GRMZM 2G040030 and comprising an A allele at position 280976157

SEQ ID NO: 2 SM6487 is a subsequence of QTL 2 located on maize chromosome 1 corresponding to GRMZM2G040030 and comprising a G allele at position 280976564

SEQ ID NO: 3 SM5343 is a subsequence of QTL 3 located on maize chromosome 1 corresponding to GRMZM2G843914 and comprising a C allele at position 281072679

SEQ ID NO: 4 SM5347 is a subsequence of QTL 4 located on maize chromosome 2 corresponding to GRMZM2G160994 and comprising an A allele at position 44262624

SEQ ID NO: 5 SM6647 is a subsequence of QTL 5 located on maize chromosome 9 corresponding to GRMZMG020721 and comprising a C allele at position 134300637

SEQ ID NO: 6 SM6652 is a subsequence of QTL 6 located on maize chromosome 9 corresponding to GRMZMG080501 and comprising an A allele at position 135348128

SEQ ID NO: 7 SM6646 is a subsequence of QTL 7 located on maize chromosome 9 corresponding to GRMZM2G080501 and comprising an G allele at position 135348898

SEQ ID NO: 8 SM5575 is a subsequence of QTL 8 located on maize chromosome 9 corresponding to GRMZM2G049322 and comprising an C allele at position 138889589

SEQ ID NO: 9 SM5572 is a subsequence of QTL 9 located on maize chromosome 9 corresponding to GRMZM2G049322 and comprising an C allele at position 138889629

SEQ ID NO: 10 SM5570 is a subsequence of QTL 10 located on maize chromosome 9 corresponding to GRMZM2G049322 and comprising an G allele at position 138889963

SEQ ID NO: 11 SM5584 is a subsequence of QTL 11 located on maize chromosome 9 corresponding to GRMZM2G049322 and comprising an G allele at position 138890220

SEQ ID NO: 12 SM6552 is a subsequence of QTL 12 located on maize chromosome 5 corresponding to GRMZM2G108716 and comprising a G allele at position 2795884

SEQ ID NO: 13 GRMZM2G040030 CDS Cold-regulated 413 plasma membrane protein 2. Upregulation of this gene is associated with drought tolerance and/or increased yield SEQ ID NO: 14 GRMZM5G843914 CDS Electron transporter. Down-regulation of this gene is associated with drought tolerance and/or increased yield SEQ ID NO: 15 GRMZM2G160994 CDS Pentatricopeptide repeat-containing protein mitochondrial. Down-regulation of this gene is associated with drought tolerance and/or increased yield SEQ ID NO: 16 GRMZM2G020721 CDS Protein REDUCED WALL ACETYLATION 2. Upregulation of this gene is associated with drought tolerance and/or increased yield SEQ ID NO: 17 GRMZM2G080501 CDS Thiaminase3, potential Gene involved in preventing damage to vitamin B1 and conserving breakdown products. Upregulation of this gene is associated with drought tolerance and/or increased yield SEQ ID NO: 18 GRMZMG049322 CDS Phosphatidylinositol N-acetyglucosaminlytransferase subunit P-related. Down-regulation of this gene is associated with drought tolerance and/or increased yield SEQ ID NO: 19 GRMZM2G108716 CDS IWS1/SPN1-transcription factor 2; Transcription factor IIS protein, potential gene involved in NUE. Upregulation of this gene is associated with drought tolerance and/or increased yield SEQ ID NO: 20 GRMZM2G040030 Protein Cold-regulated 413 plasma membrane protein 2. Upregulation of this gene is associated with drought tolerance and/or increased yield SEQ ID NO: 21 GRMZM5G843914 Protein Electron transporter. Down-regulation of this gene is associated with drought tolerance and/or increased yield SEQ ID NO: 22 GRMZM2G160994 Protein Pentatricopeptide repeat-containing protein mitochondrial. Down-regulation of this gene is associated with drought tolerance and/or increased yield SEQ ID NO: 23 GRMZM2G020721 Protein REDUCED WALL ACETYLATION 2. Upregulation of this gene is associated with drought tolerance and/or increased yield SEQ ID NO: 24 GRMZM2G080501 Protein Thiaminase3, potential Gene involved in preventing damage to vitamin B1 and conserving breakdown products. Upregulation of this gene is associated with drought tolerance and/or increased yield SEQ ID NO: 25 GRMZMG049322 Protein Phosphatidylinositol N-acetyglucosaminlytransferase subunit P-related. Down-regulation of this gene is associated with drought tolerance and/or increased yield SEQ ID NO: 26 GRMZM2G108716 Protein IWS1/SPN1-transcription factor 2; Transcription factor IIS protein, potential gene involved in NUE. Upregulation of this gene is associated with drought tolerance and/or increased yield SEQ ID NO: 27 Assay SM6492 Probe1
SEQ ID NO: 28 Assay SM6492 Primer1
SEQ ID NO: 29 Assay SM6492 Probe2
SEQ ID NO: 30 Assay SM6492 Primer2
SEQ ID NO: 31 Assay SM6487 Probe1
SEQ ID NO: 32 Assay SM6487 Primer1
SEQ ID NO: 33 Assay SM6487 Probe2
SEQ ID NO: 34 Assay SM6487 Primer2
SEQ ID NO: 35 Assay SM5343 Probe1
SEQ ID NO: 36 Assay SM5343 Primer1
SEQ ID NO: 37 Assay SM5343 Probe2
SEQ ID NO: 38 Assay SM5343 Primer2
SEQ ID NO: 39 Assay SM5347 Probe1
SEQ ID NO: 40 Assay SM5347 Primer1
SEQ ID NO: 41 Assay SM5347 Probe2
SEQ ID NO: 42 Assay SM5347 Primer2
SEQ ID NO: 43 Assay SM6647 Probe1
SEQ ID NO: 44 Assay SM6647 Primer1
SEQ ID NO: 45 Assay SM6647 Probe2
SEQ ID NO: 46 Assay SM6647 Primer2
SEQ ID NO: 47 Assay SM6652 Primer1
SEQ ID NO: 48 Assay SM6652 Probe1
SEQ ID NO: 49 Assay SM6652 Probe2
SEQ ID NO: 50 Assay SM6652 Primer2
SEQ ID NO: 51 Assay SM6646 Primer1
SEQ ID NO: 52 Assay SM6646 Probe1
SEQ ID NO: 53 Assay SM6646 Probe2
SEQ ID NO: 54 Assay SM6646 Primer2
SEQ ID NO: 55 Assay SM5575 Primer1
SEQ ID NO: 56 Assay SM5575 Probe1
SEQ ID NO: 57 Assay SM5575 Primer2
SEQ ID NO: 58 Assay SM5575 Probe2
SEQ ID NO: 59 Assay SM5572 Probe1
SEQ ID NO: 60 Assay SM5572 Primer1
SEQ ID NO: 61 Assay SM5572 Probe2

SEQ ID NO: 62 Assay SM5572 Primer2
SEQ ID NO: 63 Assay SM5570 Primer1
SEQ ID NO: 64 Assay SM5570 Probe1
SEQ ID NO: 65 Assay SM5570 Primer2
SEQ ID NO: 66 Assay SM5570 Probe2
SEQ ID NO: 67 Assay SM5584 Probe1
SEQ ID NO: 68 Assay SM5584 Primer1
SEQ ID NO: 69 Assay SM5584 Probe2
SEQ ID NO: 70 Assay SM5584 Primer2
SEQ ID NO: 71 Assay SM6552 Primer1
SEQ ID NO: 72 Assay SM6552 Probe1
SEQ ID NO: 73 Assay SM6552 Probe2
SEQ ID NO: 74 Assay SM6552 Primer2

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

The presently disclosed subject matter provides compositions and methods for identifying, selecting, and/or producing maize plants with increased drought tolerance (also referred to herein as water optimization), as well as maize plants identified, selected and/or produced by a method of this invention. In addition, the presently disclosed subject matter provides maize plants and/or germplasms having within their genomes one or more markers associated with increased drought tolerance.

To assess the value of chromosomal intervals, loci, genes or markers under drought stress, diverse germplasm was screened in controlled field-experiments comprising a full irrigation control treatment and a limited irrigation treatment. A goal of the full irrigation treatment was to ensure that water did not limit the productivity of the crop. In contrast, a goal of the limited irrigation treatment was to ensure that water became the major limiting constraint to grain yield. Main effects (e.g., treatment and genotype) and interactions (e.g., genotype x treatment) could be determined when the two treatments were applied adjacent to one another in the field. Moreover, drought related phenotypes could be quantified for each genotype in the panel thereby allowing for marker trait associations to be conducted.

In practice, the method for the limited irrigation treatment can vary widely depending upon the germplasm being screened, the soil type, climatic conditions at the site, pre-season water supply, and in-season water supply, to name just a few. Initially, a site is identified where in-season precipitation is low (to minimize the chance of unintended water application) and is suitable for cropping. In addition, determining the timing of the stress can be important, such that a target is defined to ensure that year-to-year, or location-to-location, screening consistency is in place. An understanding of the treatment intensity, or in some cases the yield loss desired from the limited irrigation treatment, can also be considered. Selection of a treatment intensity that is too light can fail to reveal genotypic variation. Selection of a treatment intensity that is too heavy can create large experimental error. Once the timing of stress is identified and treatment intensity is described, irrigation can be managed in a manner that is consistent with these targets.

I. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods. Accordingly, unless indicated to the contrary, the numerical parameters set forth in this specification and attached claims are approximations that can vary depending upon the desired properties sought to be obtained by the presently disclosed subject matter.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "allele" refers to one of two or more different nucleotides or nucleotide sequences that occur at a specific chromosome locus.

As used herein, the term "anthesis silk interval" (ASI) refers to the difference between when a plant starts shedding pollen (anthesis) and when it begins producing silk (female). Data are collected on a per plot basis. In some embodiments, this interval is expressed in days.

A "locus" is a position on a chromosome where a gene or marker or allele is located. In some embodiments, a locus may encompass one or more nucleotides.

As used herein, the terms "desired allele," "target allele", "causative allele" and/or "allele of interest" are used interchangeably to refer to an allele associated with a desired trait.

As used herein, the phrase "associated with" refers to a recognizable and/or assayable relationship between two entities. For example, the phrase "associated with a water optimization trait" refers to a trait, locus, gene, allele, marker, phenotype, etc., or the expression thereof, the presence or absence of which can influence an extent, degree, and/or rate at which a plant or a part of interest thereof that has the water optimization trait grows. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with increased drought tolerance" refers to a marker whose presence or absence can be used to predict whether and/or to what extent a plant will display a drought tolerant phenotype.

As used herein, the terms "backcross" and "backcrossing" refer to the process whereby a progeny plant is crossed back to one of its parents one or more times (e.g., 1, 2, 3, 4, 5, 6, 7, 8, 9, 10, or more). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on. In some embodiments, the number of backcrosses can be about 1 to about 10 (e.g., 1, 2, 3, 4, 5, 6, 7, 8, 9, and 10). In some embodiments, the number of backcrosses is about 7.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "elite" and/or "elite line" refer to any line that is substantially homozygous and has resulted from breeding and selection for desirable agronomic performance.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "chromosome" is used in its art-recognized meaning of the self-replicating genetic structure in the cellular nucleus containing the cellular DNA and bearing in its nucleotide sequence the linear array of genes. The *Zea mays* chromosome numbers disclosed herein refer to those as set forth in Perin et al., 2002, which relates to a reference nomenclature system adopted by L'institut National da Ia Recherché Agronomique (INRA; Paris, France).

As used herein, the phrase "consensus sequence" refers to a sequence of DNA built to identify nucleotide differences (e.g., SNP and Indel polymorphisms) in alleles at a locus. A consensus sequence can be either strand of DNA at the locus and states the nucleotide(s) at one or more positions (e.g., at one or more SNPs and/or at one or more Indels) in the locus. In some embodiments, a consensus sequence is used to design oligonucleotides and probes for detecting polymorphisms in the locus.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make up for all the genes in its genome. Genotypes can be indirectly characterized, e.g., using markers and/or directly characterized by, e.g., nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.). In some embodiments, germplasm includes but is not limited to tissue culture.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to a cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, 5, 6, 7, 8, 9, 10 or more times) to a line having a desired genetic background, selecting for the desired allele, with the result being that the desired allele becomes fixed in the desired genetic background. For example, a marker associated with drought tolerance (e.g. any markers shown in Tables 1-7) may be introgressed from a donor into a recurrent parent that is drought susceptible. The resulting offspring could then be backcrossed one or more times and selected until the progeny comprises the genetic marker(s) associated with drought tolerance in the recurrent parent background.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a yield locus (e.g. yield alleles 1-12) of the presently disclosed subject matter is linked to a marker (e.g., any of QTL 1-12) within 20, 15, 12, 10, 9, 8, 7, 6, 5, 4, 3, 2, or 1 cM of the marker. Thus, a marker linked to any one of yield alleles 1-12 may be utilized to select, identify or produce maize plants having increased tolerance to drought and/or increased yield.

In some embodiments of the presently disclosed subject matter, it is advantageous to define a bracketed range of linkage, for example, from about 10 cM and about 20 cM, from about 10 cM and about 30 cM, or from about 10 cM and about 40 cM. The more closely a marker is linked to a second locus (e.g. yield alleles 1-12), the better an indicator for the second locus that marker becomes. Thus, "closely linked" loci or markers such as a marker locus and a second locus display an inter-locus recombination frequency of about 10%, 9%, 8%, 7%, 6%, 5%, 4%, 3%, or 2% or less. In some embodiments, the relevant loci display a recombination frequency of about 1% or less, e.g., about 0.75%, 0.5%, 0.25% or less. Two loci that are localized to the same chromosome, and at such a distance that recombination between the two loci occurs at a frequency of less than about 10% (e.g., about 9%, 8%, 7%, 6%, 5%, 4%, 3%, 2%, 1%, 0.75%, 0.5%, or 0.25%, or less) can also be said to be "proximal to" each other. Since one cM is the distance between two markers that show a 1% recombination frequency, any marker is closely linked (genetically and physically) to any other marker that is in close proximity, e.g., at or less than about 10 cM distant. Two closely linked markers on the same chromosome can be positioned about 9, 8, 7, 6, 5, 4, 3, 2, 1, 0.75, 0.5 or 0.25 cM or less from each other. A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome or for example any of QTLs 1-12 as defined herein).

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., drought tolerance. The degree of linkage of a genetic marker to a phenotypic trait is measured, e.g., as a statistical probability of co-segregation of that marker with the phenotype.

Linkage disequilibrium is most commonly assessed using the measure r2, which is calculated using the formula described by Hill and Robertson, Theor. Appl. Genet. 38:226 (1968). When r2=1, complete linkage disequilibrium exists between the two marker loci, meaning that the markers have not been separated by recombination and have the same allele frequency. Values for r2 above 1/3 indicate sufficiently strong linkage disequilibrium to be useful for mapping. Ardlie et al., Nature Reviews Genetics 3:299 (2002). Hence, alleles are in linkage disequilibrium when r2 values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker", "genetic marker" "nucleic acid marker", and 'molecular marker' are used interchangeably to refer to an identifiable position on a chromosome the inheritance of which can be monitored and/or a reagent that is used in methods for visualizing differences in nucleic acid sequences present at such identifiable positions on chromosomes. Thus, in some embodiments a marker comprises a known or detectable nucleic acid sequence. Examples of markers include, but are not limited to, genetic markers, protein composition, peptide levels, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency (e.g., captured as digestibility at 24, 48, and/or 72 hours), energy yield, secondary compounds, metabolites, morphological characteristics, and agronomic characteristics. As such, a marker can comprise a nucleotide sequence that has been associated with an allele or alleles of interest and that is indicative of the presence or absence of the allele or alleles of interest in a cell or organism and/or to a reagent that is used to visualize differences in the nucleotide sequence at such an identifiable position or positions. A marker can be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS) (Rafalski and Tingey, Trends in Genetics 9:275 (1993)), an amplified fragment length polymorphism (AFLP) (Vos et al., Nucleic Acids Res. 23:4407 (1995)), a single nucleotide polymorphism (SNP) (Brookes, Gene 234: 177 (1993)), a sequence-characterized amplified region (SCAR) (Paran and Michelmore, Theor. Appl. Genet. 85:985 (1993)), a sequence-tagged site (STS) (Onozaki et al., Euphytica 138:255 (2004)), a single-stranded conformation polymorphism (SSCP) (Orita et al., Proc. Natl. Acad. Sci. USA 86:2766 (1989)), an inter-simple sequence repeat (ISSR) (Blair et al., Theor. Appl. Genet. 98:780 (1999)), an inter-retrotransposon amplified polymorphism (IRAP), a retrotransposon-microsatellite amplified polymorphism (REMAP) (Kalendar et al., Theor. Appl. Genet. 98:704 (1999)) or an RNA cleavage product (such as a Lynx tag). A marker can be present in genomic or expressed nucleic acids (e.g., ESTs). The term marker can also refer to nucleic acids used as probes or primers (e.g., primer pairs) for use in amplifying, hybridizing to and/or detecting nucleic acid molecules according to methods well known in the art. A large number of maize molecular markers are known in the art, and are published or available from various sources, such as the Maize GDB internet resource and the Arizona Genomics Institute internet resource run by the University of Arizona.

In some embodiments, a marker corresponds to an amplification product generated by amplifying a Zea mays nucleic acid with one or more oligonucleotides, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself and/or naturally occurring and/or artificial alleleic differences) as an amplification product that is generated by amplifying Zea mays genomic DNA with a particular set of oligonucleotides. In some embodiments, the amplifying is by PCR, and the oligonucleotides are PCR primers that are designed to hybridize to opposite strands of the Zea mays genomic DNA in order to amplify a Zea mays genomic DNA sequence present between the sequences to which the PCR primers hybridize in the Zea

*mays* genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the *Zea mays* genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for the detection of expressed sequence tags (ESTs) and SSR markers derived from EST sequences and randomly amplified polymorphic DNA (RAPD).

As used herein, the phrase "marker assay" refers to a method for detecting a polymorphism at a particular locus using a particular method such as but not limited to measurement of at least one phenotype (such as seed color, oil content, or a visually detectable trait); nucleic acid-based assays including, but not limited to restriction fragment length polymorphism (RFLP), single base extension, electrophoresis, sequence alignment, allelic specific oligonucleotide hybridization (ASO), random amplified polymorphic DNA (RAPD), microarray-based technologies, TAQMAN® Assays, ILLUMINA® GOLDENGATE® Assay analysis, nucleic acid sequencing technologies; peptide and/or polypeptide analyses; or any other technique that can be employed to detect a polymorphism in an organism at a locus of interest. Accordingly, in some embodiments of this invention, a marker is detected by amplifying a *Zea mays* nucleic acid with two oligonucleotide primers by, for example, an amplification reaction such as the polymerase chain reaction (PCR).

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

"Marker-assisted counter-selection" is a process by which marker genotypes are used to identify plants that will not be selected, allowing them to be removed from a breeding program or planting. Thus maize plant breeding programs may use any of the information listed in herein (e.g. a marker closely associated with any of QTLs 1-12 or any marker associated with the genes depicted in any one of SEQ ID Nos 13-19) to make marker-assisted counter-selection to eliminate maize lines or germplasm that do not have increased drought tolerance.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the term "probe" refers to a single-stranded oligonucleotide sequence that will form a hydrogen-bonded duplex with a complementary sequence in a target nucleic acid sequence analyte or its cDNA derivative. Thus, a "marker probe" and "probe" refers to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein can also be referred to as hybridization markers when located on an indel region. This is because the insertion region is, by definition, a polymorphism vis-à-vis a plant without the insertion. Thus, the marker need only indicate whether the indel region is present or absent. Any suitable marker detection technology may be used to identify such a hybridization marker, e.g., technology for SNP detection.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of the primer can depend on many factors, including, but not limited to temperature and composition (A/T vs. G/C content) of the primer. In the context of amplification primers, these are typically provided as a pair of bi-directional primers consisting of one forward and one reverse primer or provided as a pair of forward primers as commonly used in the art of DNA amplification such as in PCR amplification. As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066. Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide, which forms a stable hybrid with the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, New York, United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, California, United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least about 50%, 60%, 70%, 75%, 80%, 85%, 90% or 95% sequence identity. In some embodiments, two nucleotide sequences can have at least about 75%, 80%, 85%, 90%, 95%, or 100% sequence identity, and any range or value therein. In representative embodiments, two nucleotide sequences can have at least about 95%, 96%, 97%, 98%, 99% or 100% sequence identity, and any range or value therein.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48: 1073 (1988)). More particularly, preferred computer programs for determining sequence identity include but are not limited to the Basic Local Alignment Search Tool (BLAST) programs, which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence, BLASTX can be used to determine sequence identity; and for polynucleotide sequence, BLASTN can be used to determine sequence identity.

A "heterotic group" comprises a set of genotypes that perform well when crossed with genotypes from a different heterotic group. Hallauer et al., Corn breeding, in CORN AND CORN IMPROVEMENT p. 463-564 (1998). Inbred lines are classified into heterotic groups, and are further subdivided into families within a heterotic group, based on several criteria such as pedigree, molecular marker-based associations, and performance in hybrid combinations. Smith et al., Theor. Appl. Gen. 80:833 (1990).

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the terms "drought tolerance" and "drought tolerant" refer to a plant's ability to endure and/or thrive under drought stress or water deficit conditions. When used in reference to germplasm, the terms refer to the ability of a plant that arises from that germplasm to endure and/or thrive under drought conditions. In general, a plant or germplasm is labeled as "drought tolerant" if it displays "increased drought tolerance."

As used herein, the term "increased drought tolerance" refers to an improvement, enhancement, or increase in one or more water optimization phenotypes as compared to one or more control plants (e.g., one or both of the parents, or a plant lacking a marker associated with increased drought tolerance). Exemplary drought tolerant phenotypes include, but are not limited to, grain yield at standard moisture percentage (YGSMN), grain moisture at harvest (GMSTP), grain weight per plot (GWTPN), percent yield recovery (PYREC), yield reduction (YRED), anthesis silk interval (ASI) and percent barren (PB). Thus, a plant that demonstrates higher YGSMN than one or both of its parents when each is grown under drought stress conditions displays increased drought tolerance and can be labeled as "drought tolerant."

The phrase "abiotic stress" as used herein refers to any adverse effect on metabolism, growth, reproduction and/or viability of a plant by abiotic factors (i.e. water availability, heat, cold, etc.). Accordingly, abiotic stress can be induced by suboptimal environmental growth conditions such as, for example, salinity, water deprivation, water deficit, drought, flooding, freezing, low or high temperature (e.g., chilling or excessive heat), toxic chemical pollution, heavy metal toxicity, anaerobiosis, nutrient deficiency, nutrient excess, atmospheric pollution or UV irradiation.

The phrase "abiotic stress tolerance" as used herein refers to the ability of a plant to endure an abiotic stress better than a control plant.

As used herein "water deficit" or "drought" means a period when water available to a plant is not replenished at the rate at which it is consumed by the plant. A long period of water deficit is colloquially called drought. Lack of rain or irrigation may not produce immediate water stress if there is an available reservoir of ground water to support the growth rate of plants. Plants grown in soil with ample groundwater can survive days without rain or irrigation without adverse effects on yield. Plants grown in dry soil are likely to suffer adverse effects with minimal periods of water deficit. Severe water deficit stress can cause wilt and plant death; moderate drought can reduce yield, stunt growth or retard development. Plants can recover from some periods of water deficit stress without significantly affecting yield. However, water deficit at the time of pollination can lower or reduce yield. Thus, a useful period in the life cycle of corn, for example, for observing response or tolerance to water deficit is the late vegetative stage of growth before tassel emergence or the transition to reproductive development. Tolerance to water deficit/drought is determined by comparison to control plants. For instance, plants of this invention can produce a higher yield than control plants when exposed to water deficit. In the laboratory and in field trials drought can be simulated by giving plants of this invention and control plants less water than is given to sufficiently-watered control plants and measuring differences in traits.

As used herein, the phrase "water optimization" refers to any measure of a plant, its parts, or its structure that can be measured and/or quantified in order to assess an extent of or a rate of plant growth and development under different conditions of water availability. As such, a "water optimization trait" is any trait that can be shown to influence yield in a plant under different sets of growth conditions related to water availability. Exemplary measures of water optimization are grain yield at standard moisture percentage (YGSMN), grain moisture at harvest (GMSTP), grain weight per plot (GWTPN), and percent yield recovery (PYREC).

Water Use Efficiency (WUE) is a parameter frequently used to estimate the tradeoff between water consumption and CO2 uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of CO2 uptake to water vapor loss from a leaf or portion of a leaf, often measured over a very short time period (e.g. seconds/minutes) (Kramer, 1983, p. 406). The ratio of 13C/12C fixed in plant tissue, and measured with an isotope ratio mass-spectrometer, also has been used to estimate WUE in plants using C-3 photosynthesis (Martin et al., 1999, Crop Sci. 1775). As used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients.

As used herein, the term "gene" refers to a hereditary unit including a sequence of DNA that occupies a specific location on a chromosome and that contains the genetic instruction for a particular characteristic or trait in an organism.

The term "chromosome interval" designates a contiguous linear span of genomic DNA that resides in planta on a single chromosome. The term also designates any and all genomic intervals defined by any of the markers set forth in this invention. The genetic elements located on a single chromosome interval are physically linked and the size of a chromosome interval is not particularly limited. In some aspects, the genetic elements located within a single chromosome interval are physically linked, typically with a distance of, for example, less than or equal to 20 Mb, or alternatively, less than or equal to 10 Mb. An interval described by the terminal markers that define the endpoints of the interval will include the terminal markers and any marker localizing within that chromosome domain, whether those markers are currently known or unknown. Although it is anticipated that one skilled in the art may describe additional polymorphic sites at marker loci in and around the markers identified herein, any marker within the chromosome intervals described herein that are associated with drought tolerance fall within the scope of this claimed invention. The boundaries of chromosome intervals comprise markers that will be linked to the gene, genes, or loci providing the trait of interest, i.e. any marker that lies within a given interval, including the terminal markers that define the boundaries of the interval, can be used as a marker for drought tolerance. The intervals described herein encompass marker clusters that co-segregate with drought tolerance water optimization. The clustering of markers occurs in relatively small domains on the chromosomes, indicating the presence of a genetic locus controlling the trait of interest in those chromosome regions. The interval encompasses markers that map within the interval as well as the markers that define the terminal.

"Quantitative trait loci" or a "quantitative trait locus" (QTL) is a genetic domain that effects a phenotype that can be described in quantitative terms and can be assigned a "phenotypic value" which corresponds to a quantitative value for the phenotypic trait. A QTL can act through a single gene mechanism or by a polygenic mechanism. The boundaries of chromosome intervals are drawn to encompass markers that will be linked to one or more QTL. In other words, the chromosome interval is drawn such that any marker that lies within that interval (including the terminal markers that define the boundaries of the interval) can be used as markers for drought tolerance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

As used herein, the phrase "ILLUMINA® GOLDENGATE® Assay" refers to a high throughput genotyping assay sold by Illumina Inc. of San Diego, California, United States of America that can generate SNP-specific PCR products. This assay is described in detail at the website of Illumina Inc. and in Fan et al., 2006.

As used herein, the phrase "immediately adjacent", when used to describe a nucleic acid molecule that hybridizes to DNA containing a polymorphism, refers to a nucleic acid that hybridizes to a DNA sequence that directly abuts the polymorphic nucleotide base position. For example, a nucleic acid molecule that can be used in a single base extension assay is "immediately adjacent" to the polymorphism.

As used herein, the term "improved", and grammatical variants thereof, refers to a plant or a part, progeny, or tissue culture thereof, that as a consequence of having (or lacking) a particular water optimization associated allele (such as, but not limited to those water optimization associated alleles disclosed herein) is characterized by a higher or lower content of a water optimization associated trait, depending on whether the higher or lower content is desired for a particular purpose.

As used herein, the term "INDEL" (also spelled "indel") refers to an insertion or deletion in a pair of nucleotide sequences, wherein a first sequence can be referred to as having an insertion relative to a second sequence or the second sequence can be referred to as having a deletion relative to the first sequence.

As used herein, the term "informative fragment" refers to a nucleotide sequence comprising a fragment of a larger nucleotide sequence, wherein the fragment allows for the identification of one or more alleles within the larger nucleotide sequence.

As used herein, the phrase "interrogation position" refers to a physical position on a solid support that can be queried to obtain genotyping data for one or more predetermined genomic polymorphisms.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer to a meiotic crossover.

As used herein, the term "plant" can refer to a whole plant, any part thereof, or a cell or tissue culture derived from a plant. Thus, the term "plant" can refer to a whole plant, a plant part or a plant organ (e.g., leaves, stems, roots, etc.), a plant tissue, a seed and/or a plant cell. A plant cell is a cell of a plant, taken from a plant, or derived through culture from a cell taken from a plant.

As used herein, the term "maize" refers to a plant of the *Zea mays* L. ssp. mays and is also known as "corn."

As used herein, the term "maize plant" includes whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

As used herein, the phrase "native trait" refers to any existing monogenic or oligogenic trait in a certain crop's germplasm. When identified through molecular marker(s), the information obtained can be used for the improvement of germplasm through marker assisted breeding of the water optimization associated traits disclosed herein.

A "non-naturally occurring variety of maize" is any variety of maize that does not naturally exist in nature. A "non-naturally occurring variety of maize" can be produced by any method known in the art, including, but not limited to, transforming a maize plant or germplasm, transfecting a maize plant or germplasm and crossing a naturally occurring variety of maize with a non-naturally occurring variety of maize, through genome editing (e.g. CRISPR or TALEN), or through creating breeding stacks of desired alleles not present in nature. In some embodiments, a "non-naturally occurring variety of maize" can comprise one of more heterologous nucleotide sequences. In some embodiments, a "non-naturally occurring variety of maize" can comprise one or more non-naturally occurring copies of a naturally occurring nucleotide sequence (i.e., extraneous copies of a gene that naturally occurs in maize, such as, for Example any of the genes depicted in SEQ ID Nos: 13-19).

The "non-Stiff Stalk" heterotic group represents a major heterotic group in the northern U.S. and Canadian corn growing regions. It can also be referred to as the "Lancaster" or "Lancaster Sure Crop" heterotic group.

The "Stiff Stalk" heterotic group represents a major heterotic group in the northern U.S. and Canadian corn growing regions. It can also be referred to as the "Iowa Stiff Stalk Synthetic" or "BSSS" heterotic group.

As used herein, the term "percent barren" (PB) refers to the percentage of plants in a given area (e.g., plot) with no grain. It is typically expressed in terms of the percentage of plants per plot and can be calculated as:

$$\frac{\text{number of plants in the plot with no grain}}{\text{total number of plants in the plot}} \times 100$$

As used herein, the term "percent yield recovery" (PYREC) refers to the effect an allele and/or combination of alleles has on the yield of a plant grown under drought stress conditions as compared to that of a plant that is genetically identical except insofar as it lacks the allele and/or combination of alleles. PYREC is calculated as:

$$1 - \frac{\text{yield under full irrigation (w/allele(s) of interest)} - \text{yield under drought conditions (w/allele(s) of interest)}}{\text{yield under full irrigation (w/out allele(s) of interest)} - \text{yield under drought conditions (w/out allele(s) of interest)}} \times 100$$

By way of example and not limitation, if a control plant yields 200 bushels under full irrigation conditions, but yields only 100 bushels under drought stress conditions, then its percentage yield loss would be calculated at 50%. If an otherwise genetically identical hybrid that contains the allele(s) of interest yields 125 bushels under drought stress conditions and 200 bushels under full irrigation conditions, then the percentage yield loss would be calculated as 37.5% and the PYREC would be calculated as 25% [1.00−(200−125)/(200−100)×100)].

As used herein, the phrase "Grain Yield-Well Watered" refers to yield from an area that obtained enough irrigation to prevent plants from being water stressed during their growth cycle. In some embodiments, this trait is expressed in bushels per acre.

As used herein, the phrase "Yield Reduction-Hybrid" refers to a calculated trait obtained from a hybrid yield trial grown under stress and non-stress conditions. For a given hybrid, it equals:

$$\frac{\text{non-stress yield} - \text{yield under stress}}{\text{non-stressed yield}} \times 100.$$

In some embodiments, this trait is expressed as percent bushels per acre.

As used herein, the phrase "Yield Reduction-Inbred" refers to a calculated trait obtained from an inbred yield trial grown under stress and non-stress conditions. For a given inbred, it equals:

$$\frac{\text{non-stress yield} - \text{yield under stress}}{\text{non-stressed yield}} \times 100.$$

In some embodiments, this trait is expressed as percent bushels per acre.

As used herein, the phrase "Anthesis Silk Interval" (ASI) refers to the difference (in some embodiments, expressed in days) between when a plant starts shedding pollen (anthesis) and it starts producing silk (female). Data are collected on a per plot basis for anthesis and silking and the difference is calculated.

As used herein, the phrase "Percent Barren" refers to a percentage of plants in a given area (plot) with no grain. It is typically expressed in terms of % plants per plot and can be calculated as:

$$\frac{\text{Number of plant with no grain in a plot}}{\text{Total number of plants in the plot}} \times 100.$$

As used herein, the terms "nucleotide sequence," "polynucleotide," "nucleic acid sequence," "nucleic acid molecule" and "nucleic acid fragment" refer to a polymer of RNA or DNA that is single- or double-stranded, optionally containing synthetic, non-natural and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes soybean tissue culture from which soybean plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "reference sequence" refers to a defined nucleotide sequence used as a basis for nucleotide sequence comparison (e.g., Chromosome 1 or Chromosome 3 of *Zea mays* cultivar B73). The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in the locus or loci.

As used herein, the term "isolated" refers to a nucleotide sequence (e.g., a genetic marker) that is free of sequences that normally flank one or both sides of the nucleotide sequence in a plant genome. As such, the phrase "isolated and purified genetic marker associated with a water optimization trait in *Zea mays*" can be, for example, a recombinant DNA molecule, provided one of the nucleic acid sequences normally found flanking that recombinant DNA molecule in a naturally-occurring genome is removed or absent. Thus, isolated nucleic acids include, without limitation, a recombinant DNA that exists as a separate molecule (including, but not limited to genomic DNA fragments produced by PCR or restriction endonuclease treatment) with no flanking sequences present, as well as a recombinant DNA that is incorporated into a vector, an autonomously replicating plasmid, or into the genomic DNA of a plant as part of a hybrid or fusion nucleic acid molecule.

As used herein, the phrase "TAQMAN® Assay" refers to real-time sequence detection using PCR based on the TAQMAN® Assay sold by Applied Biosystems, Inc. of Foster City, California, United States of America. For an identified marker, a TAQMAN® Assay can be developed for application in a breeding program.

As used herein, the term "tester" refers to a line used in a testcross with one or more other lines wherein the tester and the line(s) tested are genetically dissimilar. A tester can be an isogenic line to the crossed line.

As used herein, the term "trait" refers to a phenotype of interest, a gene that contributes to a phenotype of interest, as well as a nucleic acid sequence associated with a gene that contributes to a phenotype of interest. For example, a "water optimization trait" refers to a water optimization phenotype as well as a gene that contributes to a water optimization phenotype and a nucleic acid sequence (e.g., an SNP or other marker) that is associated with a water optimization phenotype.

As used herein, the term "transgene" refers to a nucleic acid molecule introduced into an organism or its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breeding result in the artificially transferred nucleic acid molecule being present in the progeny individual.

An "unfavorable allele" of a marker is a marker allele that segregates with the unfavorable plant phenotype, therefore providing the benefit of identifying plants that can be removed from a breeding program or planting.

As used herein, the term "water optimization" refers to any measure of a plant, its parts, or its structure that can be measured and/or quantitated in order to assess an extent of or a rate of plant growth and development under conditions of sufficient water availability as compared to conditions of suboptimal water availability (e.g., drought). As such, a "water optimization trait" is any trait that can be shown to influence yield in a plant under different sets of growth conditions related to water availability.

Similarly, "water optimization" can be considered a "phenotype", which as used herein refers to a detectable, observable, and/or measurable characteristic of a cell or organism. In some embodiments, a phenotype is based at least in part on the genetic make-up of the cell or the organism (referred to herein as the cell or the organism's "genotype"). Exemplary water optimization phenotypes are grain yield at standard moisture percentage (YGSMN), grain moisture at harvest (GMSTP), grain weight per plot (GWTPN), and percent yield recovery (PYREC). It is noted that as used herein, the term "phenotype" takes into account how the environment (e.g., environmental conditions) might affect water optimization such that the water optimization effect is real and reproducible. As used herein, the term "yield reduction" (YD) refers to the degree to which yield is reduced in plants grown under stress conditions. YD is calculated as:

$$\frac{\text{yield under non-stress conditions} - \text{yield under stress conditions}}{\text{yield under non-stress conditions}} \times 100$$

Genetic loci correlating with particular phenotypes, such as drought tolerance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides chromosome intervals, QTL, Loci and genes associated with improved drought tolerance in plants (e.g. maize) and/or improved/increased yield in a plant (e.g. maize). Detection of these markers and/or other linked markers can be used to identify, select and/or produce maize plants having increased drought tolerance and/or to eliminate maize plants from breeding programs or from planting that do not have increased drought tolerance.

embodiments, all differences between two parental genotypes segregate in a mapping population based on the cross of these parental genotypes. The segregation of the different 10 markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Florida, United States of America; Zietkiewicz et al. (1994) Genomics 20:176-183.

The present invention further provides that the detecting of a molecular marker can comprise the use of a nucleic acid probe having a nucleotide base sequence that is substantially complementary to a nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a marker is designed to determine whether a particular allele of an SNP is present or absent in a particular plant.

Additionally, the methods of this invention include detecting an amplified DNA fragment associated with the presence of a particular allele of a SNP. In some embodiments, the amplified fragment associated with a particular allele of a SNP has a predicted length or nucleic acid sequence, and detecting an amplified DNA fragment having the predicted length or the predicted nucleic acid sequence is performed such that the amplified DNA fragment has a length that

TABLE 2

Yield QTLs

| Locus | Assay ID | Chromosome | Position Maize Genome V2 | Position Maize Genome V4 | Favored Allele | $\text{Log}_{10}$ (P-value) | Average increase in yield from significant tests (bushels/acre) |
|---|---|---|---|---|---|---|---|
| QTL 1 | SM6492 | 1 | 280976157 | 286079326 | A | 2.22257318 | 1.227785 |
| QTL 2 | SM6487 | 1 | 280976564 | 286079733 | G | 2.37675071 | 1.2011 |
| QTL 3 | SM5343 | 1 | 281072679 | 286174393 | C | 3.91814883 | 1.56929 |
| QTL 4 | SM5347 | 2 | 44262624 | 46120280 | A | 2.67778071 | 4.199355 |
| QTL 5 | SM6647 | 9 | 134300637 | 136753766 | C | 3.66260065 | 4.9768125 |
| QTL 6 | SM6652 | 9 | 135348128 | 137873305 | A | 4.3570016 | 4.431543 |
| QTL 7 | SM6646 | 9 | 135348898 | 137874075 | G | 3.08014297 | 7.977466667 |
| QTL 8 | SM5575 | 9 | 138889589 | 141484632 | C | 2.86646109 | 3.72865 |
| QTL 9 | SM5572 | 9 | 138889629 | 141484672 | A | 2.86646109 | 3.72864 |
| QTL 10 | SM5570 | 9 | 138889963 | 141485006 | G | 2.86646109 | 3.72865 |
| QTL 11 | SM5584 | 9 | 138890220 | 141485263 | G | 2.86646109 | 3.72865 |
| QTL 12 | SM6552 | 5 | 2795884 | 2878387 | C | 2.67985371 | 9.524465 |

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some corresponds (plus or minus a few bases; e.g., a length of one, two or three bases more or less) to the expected length based on a similar reaction with the same primers with the DNA from the plant in which the marker was first detected or the nucleic acid sequence that corresponds (e.g., a homology of at least about 80%, 90%, 95%, 96%, 97%, 98%, 99% or more) to the expected sequence based on the sequence of the marker associated with that SNP in the plant in which the marker was first detected.

The detecting of an amplified DNA fragment having the predicted length or the predicted nucleic acid sequence can be performed by any of a number or techniques, including, but not limited to, standard gel-electrophoresis techniques or by using automated DNA sequencers. Such methods of detecting an amplified DNA fragment are not described here in detail as they are well known to those of ordinary skill in the art.

II. Molecular Markers, Water Optimization Associated Loci, and Compositions for Assaying Nucleic Acid Sequences Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson, 1993; Zietkiewicz et al., 1994. The recombination frequencies of molecular markers on different chromosomes are generally 50%. Between molecular markers located on the same chromosome, the recombination frequency generally depends on the distance between the markers. A low recombination frequency typically corresponds to a small genetic distance between markers on a chromosome. Comparing all recombination frequencies results in the most logical order of the molecular markers on the chromosomes. This most logical order can be depicted in a linkage map (Paterson, 1996). A group of adjacent or contiguous markers on the linkage map that is associated with increased water optimization can provide the position of an MTL associated with increased water optimization. Genetic loci correlating with particular phenotypes, such as drought tolerance, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers can also be used by breeders to design genotypes in silico and to practice whole genome selection.

The presently disclosed subject matter provides in some embodiments markers associated with increased drought tolerance/water optimization (e.g. markers closely associated with QTLs 1-12 and/or the any one of the genes as depicted in SEQ ID Nos: 13-19). Detection of these markers and/or other linked markers can be used to identify, select and/or produce drought tolerant plants and/or to eliminate plants that are not drought tolerant from breeding programs or planting.

TABLE 3

Molecular Markers for Yield

| Assay ID | SNP Position | Favored Allele | Primer 1 | Primer 2 | Probe 1 | Probe 2 |
|---|---|---|---|---|---|---|
| SM6492 | 500 | A | SEQ ID NO. 28 | SEQ ID NO. 30 | SEQ ID NO. 27 | SEQ ID NO. 29 |
| SM6487 | 500 | G | SEQ ID NO. 32 | SEQ ID NO. 34 | SEQ ID NO. 31 | SEQ ID NO. 33 |
| SM5343 | 501 | C | SEQ ID NO. 36 | SEQ ID NO. 38 | SEQ ID NO. 35 | SEQ ID NO. 37 |
| SM5347 | 501 | A | SEQ ID NO. 40 | SEQ ID NO. 42 | SEQ ID NO. 39 | SEQ ID NO. 41 |
| SM6647 | 502 | C | SEQ ID NO. 44 | SEQ ID NO. 46 | SEQ ID NO. 43 | SEQ ID NO. 45 |
| SM6652 | 500 | A | SEQ ID NO. 47 | SEQ ID NO. 50 | SEQ ID NO. 48 | SEQ ID NO. 49 |
| SM6646 | 501 | G | SEQ ID NO. 51 | SEQ ID NO. 54 | SEQ ID NO. 52 | SEQ ID NO. 53 |
| SM5575 | 501 | C | SEQ ID NO. 55 | SEQ ID NO. 57 | SEQ ID NO. 56 | SEQ ID NO. 58 |
| SM5572 | 501 | A | SEQ ID NO. 60 | SEQ ID NO. 62 | SEQ ID NO. 59 | SEQ ID NO. 61 |
| SM5570 | 501 | G | SEQ ID NO. 63 | SEQ ID NO. 65 | SEQ ID NO. 64 | SEQ ID NO. 66 |
| SM5584 | 500 | G | SEQ ID NO. 68 | SEQ ID NO. 70 | SEQ ID NO. 67 | SEQ ID NO. 69 |

In some embodiments, a DNA sequence within 1, 2, 3, 4, 5, 6, 7, 8, 9, 10, 15, 20, or 25 cM of a marker of the presently disclosed subject matter displays a genetic recombination frequency of less than about 25%, 20%, 15%, 10%, 9%, 8%, 7%, 6%, 5%, 4%, 3%, 2%, or 1% with the marker of the presently disclosed subject matter. In some embodiments, the germplasm is a Zea mays line or variety.

DNA fragments associated with the presence of a water optimization associated trait, alleles, and/or haplotypes are also provided. In some embodiments, the DNA fragments associated with the presence of a water optimization associated trait have a predicted length and/or nucleic acid sequence, and detecting a DNA fragment having the predicted length and/or the predicted nucleic acid sequence is performed such that the amplified DNA fragment has a length that corresponds (plus or minus a few bases; e.g., a length of one, two or three bases more or less) to the predicted length. In some embodiments, a DNA fragment is an amplified fragment and the amplified fragment has a predicted length and/or nucleic acid sequence as does an amplified fragment produced by a similar reaction with the same primers with the DNA from the plant in which the marker was first detected or the nucleic acid sequence that corresponds (i.e., as a nucleotide sequence identity of more than 80%, 81%, 82%, 83%, 84%, 85%, 86%, 87%, 88%, 89%, 90%, 91%, 92%, 93%, 94%, 95%, 96%, 97%, 98%, or 99%) to the expected sequence as based on the sequence of the marker associated with that water optimization associated trait in the plant in which the marker was first detected. Upon a review of the instant disclosure, one of ordinary skill in the art would appreciate that markers that are absent in plants while they were present in at least one parent plant (so-called trans-markers), can also be useful in assays for detecting a desired trait in an progeny plant, although testing for the absence of a marker to detect the presence of a specific trait is not optimal. The detecting of an amplified DNA fragment having the predicted length or the predicted nucleic acid sequence can be performed by any of a number of techniques, including but not limited to standard gel electrophoresis techniques and/or by using automated DNA sequencers. The methods are not described here in detail as they are well known to the skilled person.

The primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including but not limited to temperature and composition (A/T vs. G/C content) of the primer.

In the context of an amplification primer, these are typically provided as one or more sets of bidirectional primers that include one or more forward and one or more reverse primers as commonly used in the art of DNA amplification such as in PCR amplification, As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing. Primers can be prepared by any suitable method. Methods for preparing oligonucleotides of specific sequence are known in the art, and include, for example, cloning, and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,068.

Primers can be labeled, if desired, by incorporating detectable moieties by for instance spectroscopic, fluorescence, photochemical, biochemical, immunochemical, or chemical moieties.

Template-dependent extension of an oligonucleotide primer is catalyzed by a polymerizing agent in the presence of adequate amounts of the four deoxyribonucleotides triphosphates (dATP, dGTP, dCTP and dTTP; i.e., dNTPs) or analogues, in a reaction medium that comprises appropriate salts, metal cations, and a pH buffering system. Suitable polymerizing agents are enzymes known to catalyze primer- and template-dependent DNA synthesis. Known DNA polymerases include, for example, *E. coli* DNA polymerase or its Klenow fragment, T4 DNA polymerase, and Taq DNA polymerase, as well as various modified versions thereof.

The reaction conditions for catalyzing DNA synthesis with these DNA polymerases are known in the art. The products of the synthesis are duplex molecules consisting of the template strands and the primer extension strands, which include the target sequence. These products, in turn, can serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension can result in the exponential accumulation of the target region defined by the primers. Sufficient cycles are run to achieve the desired amount of polynucleotide containing the target region of nucleic acid. The desired amount can vary, and is determined by the function which the product polynucleotide is to serve.

The PCR method is well described in handbooks and known to the skilled person. After amplification by PCR, the target polynucleotides can be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell, 2001. Generally, lower salt concentration and higher temperature increase the stringency of hybridization conditions.

In order to detect the presence of two water optimization associated alleles on a single chromosome in a plant, chromosome painting methods can also be used. In such methods at least a first water optimization associated allele and at least a second water optimization associated allele can be detected in the same chromosome by in situ hybridization or in situ PCR techniques. More conveniently, the fact that two water optimization associated alleles are present on a single chromosome can be confirmed by determining that they are in coupling phase: i.e., that the traits show reduced segregation when compared to genes residing on separate chromosomes.

The water optimization associated alleles identified herein are located on a number of different chromosomes or linkage groups and their locations can be characterized by a number of otherwise arbitrary markers. In the present investigations, single nucleotide polymorphisms (SNPs), were used, although restriction fragment length polymorphism (RFLP) markers, amplified fragment length polymorphism (AFLP) markers, microsatellite markers (e.g., SSRs), insertion mutation markers, sequence-characterized amplified region (SCAR) markers, cleaved amplified polymorphic sequence (CAPS) markers, isozyme markers, microarray-based technologies, TAQMAN® Assays, ILLUMINA® GOLDENGATE® Assay analysis, nucleic acid sequencing technologies, or combinations of these markers might also have been used, and indeed can be used.

In general, providing complete sequence information for a water optimization associated allele and/or haplotype is unnecessary, as the way in which the water optimization associated allele and/or haplotype is first detected-through an observed correlation between the presence of one or more single nucleotide polymorphisms and the presence of a particular phenotypic trait-allows one to trace among a population of progeny plants those plants that have the genetic potential for exhibiting a particular phenotypic trait. By providing a non-limiting list of markers, the presently disclosed subject matter thus provides for the effective use of the presently disclosed water optimization associated alleles and/or haplotypes in breeding programs. In some embodiments, a marker is specific for a particular line of descent. Thus, a specific trait can be associated with a particular marker.

The markers as disclosed herein not only indicate the location of the water optimization associated allele, they also correlate with the presence of the specific phenotypic trait in a plant. It is noted that single nucleotide polymorphisms that indicate where a water optimization associated allele is present in the genome is non-limiting. In general, the location of a water optimization associated allele is indicated by a set of single nucleotide polymorphisms that exhibit statistical correlation to the phenotypic trait. Once a marker is found outside a single nucleotide polymorphism (i.e., one that has a LOD-score below a certain threshold, indicating that the marker is so remote that recombination in the region between that marker and the water optimization associated allele occurs so frequently that the presence of the marker does not correlate in a statistically significant manner to the presence of the phenotype), the boundaries of the water optimization associated allele can be considered set. Thus, it is also possible to indicate the location of the water optimization associated allele by other markers located within that specified region. It is further noted that a single nucleotide polymorphism can also be used to indicate the presence of the water optimization associated allele (and thus of the phenotype) in an individual plant, which in some embodiments means that it can be used in marker-assisted selection (MAS) procedures.

In principle, the number of potentially useful markers can be very large. Any marker that is linked to a water optimization associated allele (e.g., falling within the physically boundaries of the genomic region spanned by the markers having established LOD scores above a certain threshold thereby indicating that no or very little recombination between the marker and the water optimization associated allele occurs in crosses, as well as any marker in linkage disequilibrium to the water optimization associated allele, as well as markers that represent the actual causal mutations within the water optimization associated allele) can be used in the presently disclosed methods and compositions, and are within the scope of the presently disclosed subject matter. This means that the markers identified in the application as associated with the water optimization associated allele are non-limiting examples of markers suitable for use in the presently disclosed methods and compositions. Moreover, when a water optimization associated allele, or the specific trait-conferring part thereof, is introgressed into another genetic background (i.e., into the genome of another maize or another plant species), then some markers might no longer be found in the progeny although the trait is present therein, indicating that such markers are outside the genomic region that represents the specific trait-conferring part of the water optimization associated allele in the original parent line only and that the new genetic background has a different genomic organization. Such markers of which the absence indicates the successful introduction of the genetic element in the progeny are called "trans markers" and can be equally suitable with respect to the presently disclosed subject matter.

Upon the identification of a water optimization associated allele and/or haplotype, the water optimization associated allele and/or haplotype effect (e.g., the trait) can for instance be confirmed by assessing trait in progeny segregating for the water optimization associated alleles and/or haplotypes under investigation. The assessment of the trait can suitably be performed by using phenotypic assessment as known in the art for water optimization traits. For example, (field) trials under natural and/or irrigated conditions can be conducted to assess the traits of hybrid and/or inbred maize.

The markers provided by the presently disclosed subject matter can be used for detecting the presence of one or more water optimization trait alleles and/or haplotypes at loci of the presently disclosed subject matter in a suspected water optimization trait introgressed maize plant, and can therefore be used in methods involving marker-assisted breeding and selection of such water optimization trait bearing maize plants. In some embodiments, detecting the presence of a water optimization associated allele and/or haplotype of the presently disclosed subject matter is performed with at least one of the markers for a water optimization associated allele and/or haplotype as defined herein. The presently disclosed subject matter therefore relates in another aspect to a method for detecting the presence of a water optimization associated allele and/or haplotype for at least one of the presently disclosed water optimization traits, comprising detecting the presence of a nucleic acid sequence of the water optimization associated allele and/or haplotype in a trait bearing maize plant, which presence can be detected by the use of the disclosed markers.

In some embodiments, the detecting comprises determining the nucleotide sequence of a *Zea mays* nucleic acid associated with a water optimization associated trait, allele and/or haplotype. The nucleotide sequence of a water optimization associated allele and/or haplotype of the presently disclosed subject matter can for instance be resolved by determining the nucleotide sequence of one or more markers associated with the water optimization associated allele and/or haplotype and designing internal primers for the marker sequences that can then be used to further determine the sequence of the water optimization associated allele and/or haplotype outside of the marker sequences.

For example, the nucleotide sequence of the SNP markers disclosed herein can be obtained by isolating the markers from the electrophoresis gel used in the determination of the presence of the markers in the genome of a subject plant, and determining the nucleotide sequence of the markers by, for example, dideoxy chain termination sequencing methods, which are well known in the art. In some embodiments of such methods for detecting the presence of a water optimization associated allele and/or haplotype in a trait bearing maize plant, the method can also comprise providing a oligonucleotide or polynucleotide capable of hybridizing under stringent hybridization conditions to a nucleic acid sequence of a marker linked to the water optimization associated allele and/or haplotype, in some embodiments selected from the markers disclosed herein, contacting the oligonucleotide or polynucleotide with digested genomic nucleic acid of a trait bearing maize plant, and determining the presence of specific hybridization of the oligonucleotide or polynucleotide to the digested genomic nucleic acid. In some embodiments, the method is performed on a nucleic acid sample obtained from the trait-bearing maize plant, although in situ hybridization methods can also be employed. Alternatively, one of ordinary skill in the art can, once the nucleotide sequence of the water optimization associated allele and/or haplotype has been determined, design specific hybridization probes or oligonucleotides capable of hybridizing under stringent hybridization conditions to the nucleic acid sequence of the water optimization associated allele and/or haplotype and can use such hybridization probes in methods for detecting the presence of a water optimization associated allele and/or haplotype disclosed herein in a trait bearing maize plant.

Particular nucleotides that are present at particular locations in the markers and nucleic acids disclosed herein can be determined using standard molecular biology techniques including, but not limited to amplification of genomic DNA from plants and subsequent sequencing. Additionally, oligonucleotide primers can be designed that would be expected to specifically hybridize to particular sequences (e.g. any sequence in proximity of the causative genes listed in Table 1) that include the polymorphisms disclosed herein In some embodiments, the marker can comprise, consist essentially of, or consist of the reverse complement of any of the aforementioned markers. In some embodiments, one or more of the alleles that make up a marker haplotype is present as described above, whilst one or more of the other alleles that make up the marker haplotype is present as the reverse complement of the allele(s) described above. In some embodiments, each of the alleles that make up a marker haplotype is present as the reverse complement of the allele(s) described above.

In some embodiments, the marker can comprise, consist essentially of, or consist of an informative fragment of any of the aforementioned markers, the reverse complement of any of the aforementioned markers, or an informative fragment of the reverse complement of any of the aforementioned markers. In some embodiments, one or more of the alleles/sequences that make up a marker haplotype is present as described above, whilst one or more of the other alleles/sequences that make up the marker haplotype is present as the reverse complement of the alleles/sequences described above. In some embodiments, one or more of the alleles/sequences that make up a marker haplotype is present as described above, whilst one or more of the other alleles/sequences that make up the marker haplotype is present as an informative fragment of the alleles/sequences described above. In some embodiments, one or more of the alleles/sequences that make up a marker haplotype is present as described above, whilst one or more of the other alleles/sequences that make up the marker haplotype is present as an informative fragment of the reverse complement of the alleles/sequences described above. In some embodiments, each of the alleles/sequences that make up a marker haplotype is present as an informative fragment of the alleles/sequences described above, the reverse complement of the alleles/sequences described above, or an informative fragment of the reverse complement of the alleles/sequences described above.

In some embodiments, the marker can comprise, consist essentially of, or consist of any marker linked to the aforementioned markers. That is, any allele and/or haplotype that is in linkage disequilibrium with any of the aforementioned markers can also be used to identify, select and/or produce a maize plant with increased drought tolerance. Linked markers can be determined, for example, by using resources available on the MaizeGDB website.

Compositions comprising a primer pair capable of amplifying a nucleic acid sample isolated from a maize plant or germplasm to generate a marker associated with increased drought tolerance are also provided. In some embodiments, the marker comprises a nucleotide sequence as set forth herein, the reverse complement thereof, or an informative fragment thereof. In some embodiments, the marker comprises a nucleotide sequence that is at least about 50%, 55%, 60%, 65%, 70%, 75%, 80%, 85%, 90%, 95% 97%, 99% or 100% identical to a nucleotide sequence set forth herein, the reverse complement thereof, or an informative fragment thereof. One of ordinary skill in the art will understand how to select alternative primer pairs according to methods well known in the art.

The identification of plants with different alleles and/or haplotypes of interest can provide starting materials for combining alleles and/or haplotypes in progeny plants via breeding strategies designed to "stack" the alleles and/or haplotypes. As used herein, the term "stacking", and grammatical variants thereof, refers to the intentional accumulation by breeding (including but not limited to crossing two plants, selfing a single plant, and/or creating a double haploid from a single plant) of favorable water optimization haplotypes in plants such that a plant's genome has at least one additional favorable water optimization haplotype than its immediate progenitor(s). Stacking includes in some embodiments conveying one or more water optimization traits, alleles, and/or haplotypes into a progeny maize plant such that the progeny maize plant includes higher number of water optimization traits, alleles, and/or haplotypes than does either parent from which it was derived. By way of example and not limitation, if Parent 1 has haplotypes A, B, and C, and Parent 2 has haplotypes D, E, and F, "stacking" refers to the production of a plant that has any of A, B, and C, with any combination of D, E, and F. Particularly, "stacking" refers in some embodiments to producing a plant that has A, B, and C as well as one or more of D, E, and F, or producing a plant that has D, E, and F as well as one or more of A, B, and C. In some embodiments, "stacking" refers to the production of a plant from a bi-parental cross that contains all water optimization associated haplotypes possessed by either parent.

III. Methods for Introgressing Alleles of Interest and for Identifying Plants Comprising the Same Markers can be used in a variety of plant breeding applications. See e.g., Staub et al., Hortscience 31:729 (1996); Tanksley, Plant Molecular Biology Reporter 1:3 (1983). One of the main areas of interest is to increase the efficiency of backcrossing and introgressing genes using marker-assisted selection (MAS). In general, MAS takes advantage of genetic markers that have been identified as having a significant likelihood of co-segregation with a desired trait. Such markers are presumed to be in/near the gene(s) that give rise to the desired phenotype, and their presence indicates that the plant will possess the desired trait. Plants which possess the marker are expected to transfer the desired phenotype to their progeny.

A marker that demonstrates linkage with a locus affecting a desired phenotypic trait provides a useful tool for the selection of the trait in a plant population. This is particularly true where the phenotype is hard to assay or occurs at a late stage in plant development. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing or imparting the trait. Having flanking markers decreases the chances that false positive selection will occur. The ideal situation is to have a marker in the gene itself, so that recombination cannot occur between the marker and the gene. Such a marker is called a "perfect marker."

When a gene is introgressed by MAS, it is not only the gene that is introduced but also the flanking regions. Gepts, Crop Sci 42:1780 (2002). This is referred to as "linkage drag." In the case where the donor plant is highly unrelated to the recipient plant, these flanking regions carry additional genes that can code for agronomically undesirable traits. This "linkage drag" can also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints. Young et al., Genetics 120:579 (1998). In classical breeding, it is usually only by chance that recombinations which contribute to a reduction in the size of the donor segment are selected. Tanksley et al., Biotechnology 7:257 (1989). Even after 20 backcrosses, one can expect to find a sizeable piece of the donor chromosome still linked to the gene being selected. With markers, however, it is possible to select those rare individuals that have experienced recombination near the gene of interest. In 150 backcross plants, there is a 95% chance that at least one plant will have experienced a crossover within 1 cM of the gene, based on a single meiosis map distance. Markers allow for unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers. See Tanksley et al., supra. When the exact location of a gene is known, flanking markers surrounding the gene can be utilized to select for recombinations in different population sizes. For example, in smaller population sizes, recombinations can be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

Of all the molecular marker types, SNPs are the most abundant and have the potential to provide the highest genetic map resolution. Bhattramakki et al., Plant Molec. Biol. 48:539 (2002). SNPs can be assayed in a so-called "ultra-high-throughput" fashion because they do not require large amounts of nucleic acid and automation of the assay is straight-forward. SNPs also have the benefit of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in various publications: Gut, Hum. Mutat. 17:475 (2001); Shi, Clin. Chem. 47:164 (2001); Kwok, Pharmacogenomics 1:95 (2000); Bhattramakki and Rafalski, Discovery and application of single nucleotide polymorphism markers in plants, in PLANT GENOTYPING: THE DNA FINGERPRINTING OF PLANTS, CABI Publishing, Wallingford (2001). A wide range of commercially available technologies utilize these and other methods to interrogate SNPs, including Masscode™ (Qiagen, Germantown, MD), Invader® (Hologic, Madison, WI), SnapShot® (Applied Biosystems, Foster City, CA), Taqman® (Applied Biosystems, Foster City, CA) and Beadarrays™ (Illumina, San Diego, CA).

A number of SNPs together within a sequence, or across linked sequences, can be used to describe a haplotype for any particular genotype. Ching et al., BMC Genet. 3:19 (2002); Gupta et al., (2001), Rafalski, Plant Sci. 162:329 (2002b). Haplotypes can be more informative than single SNPs and can be more descriptive of any particular genotype. For example, a single SNP can be allele "T" for a specific drought tolerant line or variety, but the allele "T" might also occur in the maize breeding population being utilized for recurrent parents. In this case, a combination of alleles at linked SNPs can be more informative. Once a unique haplotype has been assigned to a donor chromosomal region, that haplotype can be used in that population or any subset thereof to determine whether an individual has a particular gene. The use of automated high throughput marker detection platforms known to those of ordinary skill in the art makes this process highly efficient and effective.

The markers of the presently disclosed subject matter can be used in marker-assisted selection protocols to identify and/or select progeny with increased drought tolerance. Such methods can comprise, consist essentially of, or consist of crossing a first maize plant or germplasm with a second maize plant or germplasm, wherein the first maize plant or germplasm comprises a marker associated with increased drought tolerance, and selecting a progeny plant that possesses the marker. Either of the first and second maize plants, or both, can be of a non-naturally occurring variety of maize.

Methods for identifying a drought tolerant maize plant or germplasm can comprise detecting the presence of a marker associated with increased drought tolerance. The marker can be detected in any sample taken from the plant or germplasm, including, but not limited to, the whole plant or germplasm, a portion of said plant or germplasm (e.g., a cell from said plant or germplasm) or a nucleotide sequence from said plant or germplasm. The maize plant can be of a non-naturally occurring variety of maize. In some embodiments, the genome of the maize plant or germplasm is at least about 50%, 55%, 60%, 65%, 70%, 75%, 80%, 85%, 90%, 95%, 97%, 99% or 100% identical to that of an elite variety of maize.

Methods for introgressing an allele associated with increased drought tolerance into a maize plant or germplasm can comprise crossing a first maize plant or germplasm comprising said allele (the donor) with a second maize plant or germplasm that lacks said allele (the recurrent parent) and repeatedly backcrossing progeny comprising said allele with the recurrent parent. Progeny comprising said allele can be identified by detecting, in their genomes, the presence of a marker associated with increased drought tolerance. Either the donor or the recurrent parent, or both, can be of a non-naturally occurring variety of maize.

In some embodiments, the presently disclosed subject matter relates to the use of polymorphisms (including but not limited to SNPs) or trait-conferring parts for producing a trait carrying maize plant by introducing a nucleic acid sequence comprising a trait-associated allele and/or haplotype of the polymorphism into a recipient plant.

A donor plant, with the nucleic acid sequence that comprises a water optimization trait allele and/or haplotype can be transferred to the recipient plant lacking the allele and/or the haplotype. The nucleic acid sequence can be transferred by crossing a water optimization trait carrying donor plant with a non-trait carrying recipient plant (e.g., by introgression), by transformation, by protoplast transformation or fusion, by a doubled haploid technique, by embryo rescue, or by any other nucleic acid transfer system. Then, if desired, progeny plants comprising one or more of the presently disclosed water optimization trait alleles and/or haplotypes can be selected. A nucleic acid sequence comprising a water optimization trait allele and/or haplotype can be isolated from the donor plant using methods known in the art, and the isolated nucleic acid sequence can transform the recipient plant by transgenic methods. This can occur with a vector, in a gamete, or other suitable transfer element, such as a ballistic particle coated with the nucleic acid sequence.

Plant transformation generally involves the construction of an expression vector that will function in plant cells and includes nucleic acid sequence that comprises an allele and/or haplotype associated with the water optimization trait, which vector can comprise a water optimization trait-conferring gene. This gene usually is controlled or operatively linked to one or more regulatory element, such as a promoter. The expression vector can contain one or more such operably linked gene/regulatory element combinations, provided that at least one of the genes contained in the combinations encodes water optimization trait. The vector (s) can be in the form of a plasmid, and can be used, alone or in combination with other plasmids, to provide transgenic plants that are better water optimization plants, using transformation methods known in the art, such as the Agrobacterium transformation system. In some embodiments of the invention genes comprised in the chromosomal intervals herein may be transgenically expressed in plants to produce plants with increased drought tolerance; further, not to be limited by theory the gene models displayed in Table 9 may be transgenically expressed in plants to produce increased drought tolerant plants.

Transformed cells often contain a selectable marker to allow transformation identification. The selectable marker is typically adapted to be recovered by negative selection (by inhibiting the growth of cells that do not contain the selectable marker gene), or by positive selection (by screening for the product encoded by the selectable marker gene). Many commonly used selectable marker genes for plant transformation are known in the art, and include, for example, genes that code for enzymes that metabolically detoxify a selective chemical agent that can be an antibiotic or a herbicide, or genes that encode an altered target which is insensitive to the inhibitor. Several positive selection methods are known in the art, such as mannose selection. Alternatively, marker-less transformation can be used to obtain plants without the aforementioned marker genes, the techniques for which are also known in the art.

Water Optimization Genes

Multiple positive associations have identified the following genes as being associated with increased yield under drought: GRMZM2G040030, GRMZM5G843914, GRMZM2G160994, GRMZM2G020721, GRMZM2G080501, GRMZM2G049322, and/or GRMZM2G108716 herein "water optimization genes" (SEQ ID Nos: 13-19 respectfully).

"Linker" refers to a polynucleotide that comprises the connecting sequence between two other polynucleotides. The linker may be at least 1, 3, 5, 8, 10, 15, 20, 30, 50, 100, 200, 500, 1000, or 2000 polynucleotides in length. A linker may be synthetic, such that its sequence is not found in nature, or it may naturally occur, such as an intron.

"Exon" refers to a section of DNA which carries the coding sequence for a protein or part of it. Exons are separated by intervening, non-coding sequences (introns).

"Transit peptides" generally refer to peptide molecules that when linked to a protein of interest directs the protein to a particular tissue, cell, subcellular location, or cell organelle. Examples include, but are not limited to, chloroplast transit peptides, nuclear targeting signals, and vacuolar signals. To ensure localization to the plastids it is conceivable to use, but not limited to, the signal peptides of the ribulose bisphosphate carboxylase small subunit (Wolter et al. 1988, PNAS 85:846-850; Nawrath et al., 1994, PNAS 91:12760-12764), of the NADP malate dehydrogenase (Galiardo et al. 1995, Planta 197:324-332), of the glutathione reductase (Creissen et al. 1995, Plant J 8:167-175) or of the R1 protein Lorberth et al. (1998, Nature Biotechnology 16:473-477).

The term "transformation" as used herein refers to the transfer of a nucleic acid fragment into the genome of a host cell, resulting in genetically stable inheritance. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al 1993, Plant Cell 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen and Willmitzer 1988, Nucleic Acids Res 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extra-chromosomally, for example, as a mini-chromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Non-transformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90:217-23), spectinomycin (Svab and Maliga 1993, Plant Mol Biol 14:197-205), streptomycin (Maliga et al. 1988, Mol Gen Genet 214:456-459), hygromycin B (Waldron et al. 1985, Plant Mol Biol 5:103-108), bleomycin (Hille et al. 1986, Plant Mol Biol 7:171-176), sulphonamides (Guerineau et al. 1990, Plant Mol Biol 15:127-136), streptothricin (Jelenska et al. 2000, Plant Cell Rep 19:298-303), or chloramphenicol (De Block et al. 1984, EMBO J 3:1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. Nos. 5,561,236); aryloxy alkanoate dioxygenase or AAD-1, AAD-12, or AAD-13 which confer resistance to 2,4-D; genes such as Pseudomonas HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone); and genes conferring resistance to dicamba, such as dicamba monoxygenase (Herman et al. 2005, J Biol Chem 280:24759-24767 and U.S. Pat. No. 7,812,224 and related applications and patents). Other examples of selectable markers can be found in Sundar and Sakthivel (2008, J Plant Physiology 165:1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37:287-96). Finally, other selection systems may use hormone-free medium as the selection agent. One non-limiting example the maize homeobox gene knl, whose ectopic expression results in a 3-fold increase in transformation efficiency (Luo et al. 2006, Plant Cell Rep 25: 403-409). Examples of various selectable markers and genes encoding them are disclosed in Miki and McHugh (J Biotechnol, 2004, 107:193-232; incorporated by reference).

In some embodiments of the invention, the selectable marker may be plant derived. An example of a selectable marker which can be plant derived includes, but is not limited to, 5-enolpyruvylshikimate-3-phosphate synthase (EPSPS). The enzyme 5-enolpyruvylshikimate-3-phosphate synthase (EPSPS) catalyzes an essential step in the shikimate pathway common to aromatic amino acid biosynthesis in plants. The herbicide glyphosate inhibits EPSPS, thereby killing the plant. Transgenic glyphosate-tolerant plants can be created by the introduction of a modified EPSPS transgene which is not affected by glyphosate (for example, U.S. Pat. No. 6,040,497; incorporated by reference). Other examples of a modified plant EPSPS which can be used as a selectable marker in the presence of glyphosate includes a P106L mutant of rice EPSPS (Zhou et al 2006, Plant Physiol 140:184-195) and a P106S mutation in goosegrass EPSPS (Baerson et al 2002, Plant Physiol 129:1265-1275). Other sources of EPSPS which are not plant derived and can be used to confer glyphosate tolerance include but are not limited to an EPSPS P101S mutant from *Salmonella typhimurium* (Comai et al 1985, Nature 317:741-744) and a mutated version of CP4 EPSPS from *Agrobacterium* sp. Strain CP4 (Funke et al 2006, PNAS 103:13010-13015). Although the plant EPSPS gene is nuclear, the mature enzyme is localized in the chloroplast (Mousdale and Coggins 1985, Planta 163:241-249). EPSPS is synthesized as a preprotein containing a transit peptide, and the precursor is then transported into the chloroplast stroma and proteolytically processed to yield the mature enzyme (della-Cioppa et al. 1986, PNAS 83:6873-6877). Therefore, to create a transgenic plant which has tolerance to glyphosate, a suitably mutated version of EPSPS which correctly translocates to the chloroplast could be introduced. Such a transgenic plant then has a native, genomic EPSPS gene as well as the mutated EPSPS transgene. Glyphosate could then be used as a selection agent during the transformation and regeneration process, whereby only those plants or plant tissue that are successfully transformed with the mutated EPSPS transgene survive.

As used herein, the terms "promoter" and "promoter sequence" refer to nucleic acid sequences involved in the regulation of transcription initiation. A "plant promoter" is a promoter capable of initiating transcription in plant cells. Exemplary plant promoters include, but are not limited to, those that are obtained from plants, from plant viruses and from bacteria that comprise genes expressed in plant cells such *Agrobacterium* or *Rhizobium*. A "tissue-specific promoter" is a promoter that preferentially initiates transcription in a certain tissue (or combination of tissues). A "stress-inducible promoter" is a promoter that preferentially initiates transcription under certain environmental conditions (or combination of environmental conditions). A "developmental stage-specific promoter" is a promoter that preferentially initiates transcription during certain developmental stages (or combination of developmental stages). In some embodiments, one skilled in the art could use genome editing tools (e.g. CRISPR) to modulate natural maize promoters to up-regulate or down-regulate "water optimization genes".

As used herein, the term "regulatory sequences" refers to nucleotide sequences located upstream (5' non-coding sequences), within or downstream (3' non-coding sequences) of a coding sequence, which influence the transcription, RNA processing or stability, or translation of the associated coding sequence. Regulatory sequences include, but are not limited to, promoters, enhancers, exons, introns, translation leader sequences, termination signals, and polyadenylation signal sequences. Regulatory sequences include natural and synthetic sequences as well as sequences that can be a combination of synthetic and natural sequences. An "enhancer" is a nucleotide sequence that can stimulate promoter activity and can be an innate element of the promoter or a heterologous element inserted to enhance the level or tissue specificity of a promoter. The coding sequence can be present on either strand of a double-stranded DNA molecule, and is capable of functioning even when placed either upstream or downstream from the promoter.

Some embodiments include modulating the expression, either through direct gene or protein modification and/or via modification of native regulatory elements, of any one of: GRMZM2G040030, GRMZM5G843914, GRMZM2G160994, GRMZM2G020721, GRMZM2G080501, GRMZM2G049322, and/or GRMZM2G108716, to create plants having increased drought tolerance and/or yield.

In some embodiments, a method of selecting a first maize plant or germplasm that displays either increased yield under drought or increased yield under non-drought conditions, the method comprising: isolating nucleic acids from the first maize plant or germplasm; detecting in the first maize plant or germplasm at least one allele of a quantitative trait locus that is associated with increased yield under drought, wherein said allele is located within 50 cM, 20 cM, 10 cM, 5 cM or 1 cM from any one of yield QTL 1-12; and selecting said first maize plant or germplasm, or selecting a progeny of said first maize plant or germplasm, comprising at least one allele associated with increased yield under drought. In some embodiments, QTLs 1-12 comprise the following causative alleles:

Chromosome 1 comprising an A allele at position 280976157;
Chromosome 1 comprising a G allele at position 280976564;
Chromosome 1 comprising a C allele at position 281072679;
Chromosome 2 comprising an A allele at position 44262624;
Chromosome 9 comprising a C allele at position 134300637;
Chromosome 9 comprising an A allele at position 135348128;
Chromosome 9 comprising a G allele at position 135348898;
Chromosome 9 comprising a C allele at position 138889589;
Chromosome 9 comprising a C allele at position 138889629;
Chromosome 9 comprising a G allele at position 138889963;
Chromosome 9 comprising an G allele at position 138890220; and
Chromosome 5 comprising a G allele at position 2795884.

In some embodiments, Yield QTL 1 comprises an A at position 500 of SEQ ID NO:1, QTL 2 comprises a G at position 500 of SEQ ID NO:2, QTL 3 comprises a C at position 501 of SEQ ID NO:3, QTL 4 comprises an A at position 501 of SEQ ID NO:4, QTL 5 comprises a C at position 502 of SEQ ID NO:5, QTL 6 comprises an A at position 501 of SEQ ID NO: 6, QTL 7 comprises a G at position 501 of SEQ ID NO:7, QTL 8 comprises a C at position 501 of SEQ ID NO:8, QTL 9 comprises an A at position 501 of SEQ ID NO:9, QTL 10 comprises a G at position 501 of SEQ ID NO:10, QTL 11 comprises a G at position 500 of SEQ ID NO:11, and QTL 12 comprises a C at position 448 of SEQ ID NO:12.

In some embodiments, Maize plants comprising Yield QTL 1 can be identified with molecular assay SM6492, Yield QTL 2 can be identified with molecular assay SM6487, Yield QTL 3 can be identified with molecular assay SM5343, Yield QTL 4 can be identified with molecular assay SM5347, Yield QTL 5 can be identified with molecular assay SM6647, Yield QTL 6 can be identified with molecular assay SM6652, Yield QTL 7 can be identified with molecular assay SM6646, Yield QTL 8 can be identified with molecular assay SM5575, Yield QTL 9 can be identified with molecular assay SM5572, Yield QTL 10 can be identified with molecular assay SM5570, Yield QTL 11 can be identified with molecular assay SM5584, and Yield QTL 12 can be identified with molecular assay SM6552

In some embodiments of the invention, a plant having introduced into its genome a water optimization gene, wherein the said water optimization gene comprises 80%, 85%, 90%, 92%, 94%, 96%, 98%, or 100% sequence identity to any one of SEQ ID Nos: 13-19.

In some embodiments, said plant has increased yield as compared to a control plant.

In some embodiments, increased yield is yield under water deficit conditions.

In some embodiments a parental line of said plant was selected by or identified by a nucleotide probe or primer that annealed to any one of SEQ ID NOs: 1-12 or a closely associated marker, and said parental line conferred increased yield as compared to a plant not comprising SEQ ID NOs: 1-12.

In some embodiments said gene is introduced by heterologous expression.

In some embodiments said gene is introduced by gene editing.

In some embodiments said gene is introduced by breeding or trait introgression.

In some embodiments the nucleic acid sequence comprises any one of SEQ ID NOS: 1-12.

In some embodiments increased yield is yield under water deficit conditions.

In some embodiments said plant is maize.

In some embodiments said plant is an elite maize line or a hybrid.

In some embodiments said gene is a nucleotide sequence having 90-100% sequence homology with any one of SEQ ID NOs: 1-12.

In some embodiments said plant also comprises at least one Haplotypes A-M.

In some embodiments said plant also comprises at least one marker selected from the group comprised of markers SM2973, SM2980, SM2982, SM2984, SM2987, SM2991, SM2995, and SM2996.

In some embodiments a plant cell, germplasm, pollen, seed or plant part from the plant of any one of the previous embodiments is provided.

In some embodiments a genotyped plant, plant cell, germplasm, pollen, seed or plant part selected or identified based on the detection of any one of SEQ ID NOs: 1-12 or QTLs 1-12 is provided.

In some embodiments of the invention, the plant, plant cell, germplasm, pollen, seed or plant part is genotyped by isolating DNA from said plant, plant cell, germplasm, pollen, seed or plant part and DNA is genotyped using either PCR or nucleotide probes that adhere to any one of SEQ ID NOs 1-12 or QTLs 1-12.

Haplotypes A, B, C, D, E, F, G, H, I, J, K, and M are described in U.S. Pat. No. 8,822,755 which is incorporated by reference. Markers SM2973, SM2980, SM2982, SM2984, SM2987, SM2991, SM2995, SM2996 are described in patent application WO2017106274 which is incorporated by reference.

Thus, the presently disclosed subject matter provides in some embodiments inbred *Zea mays* plants comprising one or more alleles associated with increased yield, increased yield under drought, or a desired water optimization trait.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

To assess the value of alleles under drought stress, diverse germplasm was screened in controlled field-experiments comprising a full irrigation control treatment and a limited irrigation treatment. The goal of the full irrigation treatment is to ensure water does not limit the productivity of the crop. In contrast, the goal of the limited irrigation treatment is to ensure that water becomes the major limiting constraint to grain yield. Main effects (e.g., treatment and genotype) and interactions (e.g., genotype x treatment) can be determined when the two treatments are applied adjacent to one another in the field. Moreover, drought related phenotypes can be quantified for each genotype in the panel thereby allowing for marker-trait associations to be conducted.

In practice, the method for the limited irrigation treatment can vary widely depending upon the germplasm being screened, the soil type, climatic conditions at the site, pre-season water supply, and in-season water supply, to name just a few. Initially, a site is identified where in-season precipitation is low (to minimize the chance of unintended water application) and is suitable for cropping. In addition, determining the timing of the stress can be important, such that a target is defined to ensure that year-to-year, or location-to-location, screening consistency is in place. An understanding of the treatment intensity, or in some cases the yield loss desired from the limited irrigation treatment, can also be considered. Selection of a treatment intensity that is too light can fail to reveal genotypic variation. Selection of a treatment intensity that is too heavy can create large experimental error. Once the timing of stress is identified and treatment intensity is described, irrigation can be managed in a manner that is consistent with these targets.

General methods for assessing and assessing drought tolerance can be found in Salekdeh et al., 2009 and in U.S. Pat. Nos. 6,635,803; 7,314,757; 7,332,651; and 7,432,416.

Example 1 Panels

This set of markers leverages three panels of materials. The first is a Linkage Disequilibrium, LD, panel. It is comprised of 210 stiff stalk (SS) and 294 non-stiff stalk (NSS) materials primarily from North America. The second panel is a mid-maturity North American Family Based Association Mapping, FBAM, panel. It is comprised of 72 bi-parental populations using 47 parents. Parents for each cross are from the same heterotic group. The NSS heterotic group is made up of 47 populations from 24 parents with 1198 DH progeny. The SS heterotic group is made up of 25 populations from 23 parents with 713 DH progeny. The third panel is a late maturity North American and European FBAM panel (NEFBAM). It is comprised of 104 bi-parental populations using 53 parents. The NSS heterotic group is made up of 50 populations from 19 parents with 865 DH progeny. The SS heterotic group is made up of 54 populations from 34 parents with 864 DH progeny. One marker was originally identified using the LD panel information that was originally used to identify Artesian 2. It was missed initially because of incorrect genotypic information for the marker. The remaining markers were identified using the FBAM panel. The LD and NEFBAM panels were used to validate results found in the FBAM panel.

Example 2 Genotypic Data

Initial data for the FBAM and NEFBAM panels was generated using a reduced representation sequencing method that preferentially sequences gene rich regions. Global read depth was approximately 1×, however, gene rich regions were close to 10× while other regions were close to 0×. Genotypes for the LD panel were generated via transcriptome sequencing with low read depth. Markers with more than 20% missing calls across the panel parents were removed from analysis. Those with less than 20% missing calls were imputed based the CINPUTE++ algorithm and then projected from parents to DH progeny using a common set of chip based markers. After the initial testing, assays were generated for the highest confidence markers. The FBAM and NEFBAM parents were then re-genotyped using the assays. Progeny genotypes were once again projected using the new parent genotypes and re-analyzed using the corresponding phenotypic information in order to validate the original results.

Example 3 Phenotypic Data

Yield under limited water conditions was measured at the plot level and converted to bushels/acre. Two types of environments were used in the analysis: managed and target stress. Managed stress locations were in regions that received very little annual rainfall. Irrigation was severely reduced approximately two weeks before flowering and continued at a reduced level until approximately two weeks after flowering. Target stress locations were in target market regions which historically underwent season long drought stress. Control plots under full irrigation were used to evaluate the level of stress in terms of yield reduction at both types of locations. DH progeny were tested as inbreds using only the FBAM panel. DH progeny were crossed to common testers and tested as hybrids for all three panels. The LD panel used a single tester per heterotic group, while both the FBAM and NEFBAM panels used two testers per heterotic group.

Example 4 Models

In order to assess the best method to identify marker trait associations, multiple models were used to analyze the data:
1) Yield=$\mu$+Population+Marker+Population*Marker+$\varepsilon$, where & is a random effect and all other terms are fixed effects
2) Yield=$\mu$+Population+Marker+Population*Marker+$\varepsilon$, where Population, Population*Marker and & are random effects and all other terms are fixed effects
3) Yield=$\mu$+Kinship+Marker+$\varepsilon$, where Kinship and ¿ are random effects and all other terms are fixed effects
4) Yield=$\mu$+Kinship+Marker+location+$\varepsilon$, where Kinship and & are random effects and all other terms are fixed effects
5) Yield=$\mu$+Kinship+Marker+location+tester+$\varepsilon$, where Kinship and & are random effects and all other terms are fixed effects In all cases m represents the overall mean and e represents error with a N (0,1) distribution.

FBAM analyses were run using all of the models. LD panel analyses only used model 3. NEFBAM analyses were run using only model 5. All analyses were run for each heterotic group and environment type (managed or target stress) separately.

Example 5 MTA Results

MTAs were initially identified based on results from a subset of the LD panel markers using transcriptome based genotypes and all of the FBAM panel markers using reduced representation sequencing based genotypes. MTAs identified are found in TABLE 2. Markers were prioritized based on results from these analysis. Assays were generated based on the top priority markers and used to re-genotype the parents. Examples of assays are found in TABLE 3. Once re-genotyped, the parents were used to project genotype information to progeny again using the chip-based genotypes as anchors. Analyses using the assay-based genotypes were completed using models 3-5 for the FBAM and NEF-BAM panels. Twelve marker trait associations (MTAs) were selected after validation with a−log (P-value)>2 for multiple location/tester combinations and multiple panels within the same heterotic group. Additionally, favorable alleles for these MTAs did not display significant adverse effects across any tests for the specific heterotic group. These represent the highest confidence markers based on the collected results.

Example 6: Introgression of Yield QTLs Using Molecular Markers

QTLs associated with yield are introgressed into corn plants by methods known to those skilled in the art of plant breeding. A plant breeder uses molecular markers to monitor the introgression of yield QTLs by identifying plants with the yield QTL and selecting lines carrying the favorable allele for one or more of said molecular markers.

That which is claimed:

1. A method of selecting a first maize plant or germplasm that displays either increased yield under drought or increased yield under non-drought conditions, the method comprising:
   a) isolating nucleic acids from the first maize plant or germplasm;
   b) detecting in the first maize plant or germplasm at least one allele of a quantitative trait locus that is associated with increased yield under drought or non-drought conditions, wherein said allele is located within 10 cM, 5 CM or 1 cM from yield QTL 6 which comprises an A at position 501 of SEQ ID NO:6, which corresponds to Chromosome 9 comprising an A allele at position 135348128;
   c) selecting said first maize plant or germplasm, or selecting a progeny of said first maize plant or germplasm, comprising at least one allele associated with increased yield under drought or non-drought conditions; and,
   d) crossing said selected first maize plant or germplasm with a second maize plant or germplasm to produce an introgressed maize plant or germplasm comprising said QTL 6, wherein the introgressed maize plant or germplasm displays increased yield under drought and non-drought conditions as compared to a maize plant or germplasm not comprising said QTL 6.

2. The method of claim 1, wherein the at least one allele is detected using a composition comprising a detectable label.

3. A method introgressing a water optimization locus into a maize plant, said method comprising:
   a) isolating a nucleic acid from a first population of maize plants;
   b) detecting in said nucleic acid the presence of at least one allele of a quantitative trait locus that is associated with increased yield under drought conditions, wherein said allele is located within 10 cM, 5 cM or 1 cM from yield QTL 6, and wherein said QTL6 comprise an A at position 501 of SEQ ID NO:6 which corresponds to Chromosome 9 comprising an A allele at position 135348128;
   c) selecting one or more plants with the water optimization locus from the first population of maize plants; and d) producing offspring from the one or more plants with the water optimization locus selected in c) by crossing the selected plants with a second maize population not having the water optimization locus, wherein the offspring exhibit improved water optimization as compared to the first population.

4. The method of claim 3, wherein the at least one allele is detected by the genetic marker of SEQ ID NO: 6.

5. The method of claim 3, wherein the maize plant belongs to the non-stiff stalk heterotic group.

6. The method of claim 3, wherein said marker is associated with the presence of a water optimization gene comprising SEQ ID NO: 17 and a gene encoding a protein comprising SEQ ID NO: 24.

7. The method of claim 3, wherein the maize plant belongs to the stiff stalk heterotic group.

8. The method of claim 3, wherein the maize plant is a hybrid maize plant and/or an elite maize plant.

9. A plant having introduced into its genome a water optimization gene and a yield allele wherein said water optimization gene comprises a nucleotide sequence encoding at least one polypeptide comprising SEQ ID NO: 24 and the yield allele is SEQ ID NO: 6.

10. The plant of claim 9, wherein said plant has increased yield as compared to a control plant.

11. The plant of claim 10, wherein increased yield is yield under water deficit conditions.

12. The method of claim 1, wherein a parental line of said first maize plant was selected by or identified by a nucleotide probe or primer that annealed to SEQ ID NO: 6 and said parental line conferred increased yield as compared to a plant not comprising SEQ ID NO: 6.

13. The plant of claim 9, wherein said gene is introduced by heterologous expression.

14. The plant of claim 9, wherein said gene is introduced by gene editing.

15. The plant of claim 9 wherein said gene is introduced by breeding or trait introgression.

16. The plant of claim 9, wherein said plant is maize.

17. The plant of claim 16, wherein said plant is an elite maize line or a hybrid.

* * * * *

SEQUENCE LISTING

```
<160> NUMBER OF SEQ ID NOS: 74

<210> SEQ ID NO 1
<211> LENGTH: 1000
<212> TYPE: DNA
<213> ORGANISM: Zea mays
<220> FEATURE:
<221> NAME/KEY: misc_feature
<222> LOCATION: (500)..(500)
<223> OTHER INFORMATION: n is a, t, g, or c

<400> SEQUENCE: 1
aaagtatcag gtgtgaatga atttataagc tattttcacc tgacactggt aggaccattt      60
tgtaaggtat ttctcactac caattaatcg atgacaactc tgttctattc cactacaggt     120
atctcttgat attggatcgc acaaattgga agaccaacat gctgacagct ctcttggttc     180
cttacatttt cttcaccctg cctaatgtgc tgttttctct gatcaggtga ttaggcgcat     240
caaccctatc tcacttacca atccattgtg tattgtatgg atcaattgtt agttaccatg     300
atagtttttt tgtcacaatg ggcagaagca tatgtgactg atgtacagta aacttgtagg     360
atcaaagcat ttcaaataca atgttgtcat actctacgct tcgtagaatg acagttacaa     420
agcgtatcaa attagttatg ttttttttgga tcagttgctg taggacttca gtattggtta     480
catgttgatg tgaatcgaan tcgatcttat ttatgatttc ctgtgaatca attaatgtag     540
gacttgcatg ttggttactt gttgatgtga agtatgctgt agtggtagct caaaacgctt     600
tcaggagaga atgttctctc ttgaccactt gatctataac agagaatatg aaagtaaaat     660
atcttatatc atcaagcctt tgaattttca gaggagaggt ggggaaatgg attgcgatta     720
ttgctgttat tctgcgtcta ttctttccac gacacttccc aggtacatct ccagtactat     780
tttgcatcct atcaaatctc cagatattgg tatacattta ccctttatt  aacattttgc     840 agttttgccc ttaacataaa ataatcacag ttcatccttt tgcttggtga ctctgaacat     900
tgtttcgtcc tgtgcaccag attggttaga gcttcctggt tccatcatcc tgctcacagt     960
ggtcgcccct agcctgttcg cggacagctt caggggagac                          1000

<210> SEQ ID NO 2
<211> LENGTH: 1000
<212> TYPE: DNA
<213> ORGANISM: Zea mays
<220> FEATURE:
<221> NAME/KEY: misc_feature
<222> LOCATION: (500)..(500)
<223> OTHER INFORMATION: n is a, c, g, or t

<400> SEQUENCE: 2
atgacagtta caaagcgtat caaattagtt atgttttttt ggatcagttg ctgtaggact      60
```

```
tcagtattgg ttacatgttg atgtgaatcg aaatcgatct tatttatgat ttcctgtgaa    120
tcaattaatg taggacttgc atgttggtta cttgttgatg tgaagtatgc tgtagtggta    180
gctcaaaacg ctttcaggag agaatgttct ctcttgacca cttgatctat aacagagaat    240
atgaaagtaa aatatcttat atcatcaagc ctttgaattt tcagaggaga ggtggggaaa    300
tggattgcga ttattgctgt tattctgcgt ctattctttc cacgacactt cccaggtaca    360
tctccagtac tattttgcat cctatcaaat ctccagatat tggtatacat ttacccttt     420 attaacattt tgcagttttg cccttaacat aaaataatca cagttcatcc ttttgcttgg    480
tgactctgaa cattgtttcn tcctgtgcac cagattggtt agagcttcct ggttccatca    540
tcctgctcac agtggtcgcc cctagcctgt tcgcggacag cttcagggga gacctcgttg    600
gtgtcttcat atgccttgtg atcggatgct acctgctcca agaacacatc aaggcgtcag    660
gtggattcag gaacgcctttc aggaagggca atggtgtgtc caactccatc ggcatcctcc    720
tgctcttcat ctaccctgtc tgggccggtg tgctgcaagt cctgtaggca ccattgcctc    780
agtgtttccc ctgtgcggtc cagctccgtt cccgttcgtg cccgtgcaaa tgttccctct    840
atggtgatcc gtgatcctgt gtcacgagta ggtgatgttt ttatgtgtgc ttgagttgat    900
cggttgggca tgttgccatg ttggtggaca gttttgttta tctcatttgt tgtagttcga    960
tgtcagcatt tggttcgttc gagtacataa acgccaataa                         1000

<210> SEQ ID NO 3
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is A, T, C, or G

<400> SEQUENCE: 3
tctcaaggtg ctttgtgctc ccctcccggg ttgagcttcc ttagtgatat cacatttgac     60
cttagctttt accacttcct gtgaaggaaa gattaaacac aaatcactca aaactgcagg    120
aagtaacgta gcgagaggtg ggaaccatgc atttactgag cggtacaata tggatgagca    180
cgcaggagga ggatgttttt tttaccggca taggtagaac aatcgtcttg tctgaagaac    240
gcaaagcgtc tgtagcatac atatcctcaa aatatctgcc actggaaaaa cattaatcgc    300
attttgagca ttgttccatc tgaaccctcc ctccccaaaa aaaaaaaaaa aaaaactacg    360
cagaagcctg cagacaccaa cctcgtggat cgcttgtacc gctcggaaga gccgaaagat    420
ttcatcgcct tggcaaaagc tgcgtgcccc ttcttctcca gagcctccac ctccatgccg    480
cggcagagct aagagtcaat naagaactga aatttaaaaa aaaatatgca aacgagtcta    540
agccagtaag acaccgagca aacagcgacg gagacgaaga agagaaacaa gggctcacag    600
agatcagctg tagttgccca gtggtcagcg cccggaaact cggtagcagg gacagggaca    660
gggaggaaga aggcgagcac gagggagggg gctccggtcg tcgacccaag accaagcagc    720
caggcaggca aacggcgtct tctgatgaag tcacgctaag ctccaaggaa cccagcactg    780
tccacaccga cgagtgccat ctatctctat ctctacccgc accaccaccc tccactcttc    840
cggtcaagag ctaaatgagc catttggaga ggaaaacgga aagcaaagcc ctctctctct    900
ctgtgtgtgt ccccgatcca actgctctgc atccacccc actgagcact gcgtctgcgt    960
gtgtatgtgc atatatacag cacaagcgag cgccaacgct a                       1001
```

<210> SEQ ID NO 4
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a, c, g, or t

<400> SEQUENCE: 4

```
taagggacat ctggaggtcc atggtggcga cctcgcagtc gcagtcgcag cagcagcagc      60
gcatgacgag ccggaactac gtctgcgtgg tctcgtccta cctggcgtgc gggcggctgg     120
aggatgccgg ggaggtcgtc gaccagtggc agcgctctaa ggcccccgag ttcgacgtct     180
ccgcctgcaa ccggctgctg gacgccctcc tgcgcgccgg tctcgccgac gccgcgggta     240
ggtttcggga gctgatgctg cagaagcgtt gtatactgac tagcagcagc agcagcaggg     300
cggcagtggt cgagtgatta cgggttggtt tcgagtctgt tcttttttgtt gttgttgtct     360
tgtgtgaagg aataaacaat ggacagccca agcactctgc acgttacgtt attctctgac     420
atgattgatg tgatcatgtc tggttagtgg gttacgtacg tacatagtgc caggctcgtg     480
gcatgacgaa gcacactgag naactgtgta cggccatcgg tgcgcgcgtt cttgtgacct     540
tcgtcttctt cctggcccta actaccctgc aggctgcagc tattgtaaag acgacaggta     600
cagcggctac gagctggcgg aaacgatgct gttgcatact gtttgtccta tgctccacat     660
tctcgccacg aagatggtga cgttgcgagt tgttgtttca tgattgtgcg tggaataaag     720
ataccggtcg caagccacag gagttttttc aagtatttcg agtcctttca tgcgttgcct     780
accaccacct tccattccat ccacggctgc tttgatagcc cccgaaacct cagaatactc     840
ccggtcccgg cccggtgtca aacactcggc acacgcctgc ctgccatccg ccgctccttc     900
ggcacagtcg cgctcgcgca gatgtaaaac gtgccaaccc tgcgtcaaag atccacccag     960
atgcaggaac tgaactaggc gggtctggga tcggcaagaa a                         1001
```

<210> SEQ ID NO 5
<211> LENGTH: 1002
<212> TYPE: DNA
<213> ORGANISM: Zea mays
<220> FEATURE:
<221> NAME/KEY: misc_feature
<222> LOCATION: (502)..(502)
<223> OTHER INFORMATION: n is A, T, C or G

<400> SEQUENCE: 5

```
aaattataaa tttacaattt ctcaatatca gtatccgaag gcattgtgtc tctaacaaaa      60
agaaaatgtt gggttcaaca gacttatatt catggaccag ttgcttcttc tggagaatcg     120
tttaacactg agggcattgt aagctacagt tgctctcctc caatcattca agcttcctag     180
ttgcactatt ctgctaactg ggttgcaatt atgttttcag atctgaattt ggaggttatc     240
tactttattt ttacatatgt gatcgtacaa acttgcttgg agagtctgcc aaggtactgt     300
tgtgcagata ttgttacaga gtctggtcat atgcctttgt gtaaaattgc catttattag     360
aacctttcaa attttctgaa gtattcagat tgatgaaaaa atatcccagt gcattcttca     420
tgtgccatta tatatagtgt aacactttaa tccactaacc tttttattgg tatgcttcat     480
ctgcagaatt acagccgaga tntgttcctt ttcctctact ttcttcttat cattgtagca     540
gctatgactt cctttaaggt ccatcaagac aagtcatcat tcacaggaaa atctgtactg     600
tacttgaata ggcatcaaac tgaagaatgg aagggttgga tgcaggtact tatcatactt     660
```

```
ttatcttcct cctgcagtgt ttcctgggtc tcagaaacga ttttttttaat aattgcccat    720 aaacatagtt tagtgagtag ctacagttcg tgtatgagca ttgatacatc agaactatag    780
aagttggtgt gtgcagttat aagcatctgc tctcatctgg cacagctacc atagtagcat    840
gtatgattta tcacctcttg ctggtccatt catggttatg catctctctt gggttgcaaa    900
aaagctaatt ataagtcaca cctattaatt gacaaatatg gggtttcacc tgtcttagca    960
ccaaagtttt gccatgctga ctcaccacac tgccttgtga ag                      1002
```

<210> SEQ ID NO 6
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a, c, g, or t

<400> SEQUENCE: 6

```
atatttagct tctaggttgt attatacacc ttttcagcgg ccttttatac ttgagttgga    60
ggactacaag ataaagtgtg gatatctcaa agggctcggc tgcagttttg cctgtggtca    120
atggtcgtcg cttcattggt caaaccttga gaccccggt tcagcaatcg cagttccaca    180
aggcggcgat ggacggcggc ggggtcgata cggccacgac ggcggcctgg atggagaagc    240
accggcacat gtacgagcgg gccacccggc acccgttcac cgtctccatc cgcgacggta    300
ccgtcgacat gtctgccttc aagcgctggc tggtcagtct caatccctct attttcccca    360
acaactgatg cagtgatgtt ctcgtcgtga cgtcgtgtaa caccttcaac tgcagaaaat    420
tgaagtggct aagctttgac cttttcatgt ctgattcttg gttcgtggtg tcggcatcg    480 agatctgtac atcaatctaa ntactaccaa gaagtcttgg agttgctacc aagttaacaa    540
aaattagtgt gcacggctat gaaattgagt gactagttgc gtgattcgag tcagaggtgt    600
ttctgggaga actgtgaatt taaaattgaa cctgaaagcg tgaaggcaaa cgatctttat    660
cggcatatac tgatactgcg tctgtgaaga tcttgtgttt ccagtggact agtcactctg    720
aatgttgtta ttctgctgtt gcttcctgtt gacaaaaata actccagaat agaattggct    780
cttagttgac actgtccaat tatgatagta taaagtgatg aaggatcttg ttcagagaac    840
tgtgcaaaaa agaactcaac tgagtcaact cctagttgag catagtattc tgtaattttt    900
ttttaaaagt tactctatat gatcttgggt tctttttcta gttgaaagca ttttggttgg    960
tcataattac agctgtctac acaatgatca atatgtgctg g                       1001
```

<210> SEQ ID NO 7
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: N is A, T , C or G

<400> SEQUENCE: 7

```
tcgttcgatt atttgcgtag atgtttggac tcagagaaca cgctggtaat taggaccgag    60
aagagctcat atcccagaaa ccaatttcca gctcgagtac ccggacgaag gcctcttcag    120
cactctggac agcatcagcc ggtgcgttag ccaagcaacg atccacgatg ctctgcagag    180
actggcagta ctgtctgaac ccggcgctgc cccatctctg gcaggtgccc aggagctccg    240
```

```
gcggcgtctt gttgccgtct tgtatgcaga aaccaaagct gtcctggtac acggtttcga    300
tcgtccagaa ggtagttaca gcaacagcat agctaatctc tggctcagta aagctccgga    360
gaaacctggc aacaaggaca ttgccggtta tagatcttca gtcatgctca tgctactgtg    420
tgggaacttt tcgaacgtac ggacaagacg aacctgtggt actctagatt ggcttttaag    480
ggggaaacac ttgctagatc nacgccccat acagtagctt cgttcttgaa ccaagagatc    540
tcgtcgctga tagacgctac tccacccagg atgatttcca tgtccgagct gtcttcttgc    600
ttgcagcatt tgagcagtac acttgctatg aatgcaacaa attcccttac aaacagatag    660
tcctggctct gcatatgacg aagaaaccag tctgtttatt ttttttctcc cctcatggta    720
ctcataacca aaatgaaatt tatttaagaa atcacggaa agaaaattag ccagcacata    780
ttgatcattg tgtagacagc tgtaattatg accaaccaaa atgctttcaa ctagaaaaag    840
aacccaagat catatagagt aactttaaa aaaaaattac agaatactat gctcaactag    900
gagttgactc agttgagttc ttttttgcac agttctctga acaagatcct tcatcacttt    960
atactatcat aattggacag tgtcaactaa gagccaattc t                       1001
```

<210> SEQ ID NO 8
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: N is A, T, C or G

<400> SEQUENCE: 8

```
atcagaagaa tttaatgaga cacttgatgc cctggtatct aacagtgacc ttttgttgga     60
ttttcttcaa aattttgatc ctgctgtcat aagggaccta cataatcatg gttctccatc    120
ctctaccgca aactgcatca caatattgaa gccatctcga agaaatcaat ttattgacat    180
ggacaatatt tatccgcaag agaaaggaac cgagagcatc ttcaacgagc aaatggaagg    240
gaaacattct ttatggaagc catattctaa tgtgcccttg cagtccctaa agaagattc    300 ttgttcatca aggcagaaac tgtcaaggtc cagtcaccaa gaaaatactg gaaaacgtgg    360
ctcccccacc cggattgttg tcttgaagcc aaatcttgag aaacctcatg atattgaaga    420
agcccttccc ctacatcata aaatatccca ttctgattat agaaggcata agaatgtcc    480 ggaggttgat agatggactc naaatactga agattacatg tgtcaggtgc cccttggaga    540
ttctgaaaca ttaagtcgta tggggaaggg atctagagaa attgctaggg agatcaccaa    600
acagatgaga gctgctaggg gtggaagtag gaaacattct gtcaaaccgg agactagaac    660
tcttgcttca gatgaaaggt cacagtttcg gtcatctgtt actagaccca agactccaga    720
gtcaattcat agatattctg agtcatgtga tgcttgggct tcttcaagtc tcaactcttt    780
gccaacatat tcgactgaaa catcagaaag caaggaagca agaaacacc tctctaacag    840 atggaagaag acccgtcagt gtcagcatca agaaactgat aatgacagct tcaacacgct    900
tggggatatg cttgctctct ctgatcagaa tgcatcaaat gttgctaccc ataaaatgac    960
atgcaggaaa tgtccaaagt cagaagtgca gagtgataga a                       1001
```

<210> SEQ ID NO 9
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: n is a, c, g, or t

<400> SEQUENCE: 9

```
tggatgctaa gcgtctttct attgatgaat cccttcacat atcagaagaa tttaatgaga      60
cacttgatgc cctggtatct aacagtgacc ttttgttgga ttttcttcaa aattttgatc     120
ctgctgtcat aagggaccta cataatcatg gttctccatc ctctaccgca aactgcatca     180
caatattgaa gccatctcga agaaatcaat ttattgacat ggacaatatt tatccgcaag     240
agaaaggaac cgagagcatc ttcaacgagc aaatggaagg gaaacattct ttatggaagc     300
catattctaa tgtgcccttg cagtcccgtaa aagaagattc ttgttcatca aggcagaaac    360
tgtcaaggtc cagtcaccaa gaaaatactg gaaaacgtgg ctcccccacc cggattgttg     420
tcttgaagcc aaatcttgag aaacctcatg atattgaaga agcccttccc ctacatcata     480
aaatatccca ttctgattat ngaaggcata agaatgtcc ggaggttgat agatggactc      540
caaatactga agattacatg tgtcaggtgc cccttggaga ttctgaaaca ttaagtcgta     600
tggggaaggg atctagagaa attgctaggg agatcaccaa acagatgaga gctgctaggg     660
gtggaagtag gaaacattct gtcaaaccgg agactagaac tcttgcttca gatgaaaggt     720
cacagtttca gtcatctgtt actagaccca agactccaga gtcaattcat agatattctg     780
agtcatgtga tgcttgggct tcttcaagtc tcaactcttt gccaacatat tcgactgaaa     840
catcagaaag caaggaagca agaaacacc tctctaacag atggaagaag accgtcagt     900
gtcagcatca agaaactgat aatgacagct caacacgct tggggatatg cttgctctct     960
ctgatcagaa tgcatcaaat gttgctaccc ataaaatgac a                        1001
```

<210> SEQ ID NO 10
<211> LENGTH: 1001
<212> TYPE: DNA
<213> ORGANISM: Zea mays
<220> FEATURE:
<221> NAME/KEY: misc_feature
<222> LOCATION: (501)..(501)
<223> OTHER INFORMATION: N is A, T, C or G

<400> SEQUENCE: 10

```
cttccacccc tagcagctct catctgtttg gtgatctccc tagcaatttc tctagatccc      60
ttccccatac gacttaatgt ttcagaatct ccaaggggca cctgacacat gtaatcttca     120
gtatttggag tccatctatc aacctccgga cattctttat gccttctata atcagaatgg     180
gatattttat gatgtagggg aagggcttct tcaatatcat gaggtttctc aagatttggc     240
ttcaagacaa caatccgggt gggggagcca cgttttccag tattttcttg gtgactggac     300
cttgacagtt tctgccttga tgaacaagaa tcttctttta gggactgcaa gggcacatta     360
gaatatggct tccataaaga atgtttccct tccatttgct cgttgaagat gctctcggtt     420
cctttctctt gcggataaat attgtccatg tcaataaatt gatttcttcg agatggcttc     480
aatattgtga tgcagtttgc ngtagaggat ggagaaccat gattatgtag gtcccttatg     540
acagcaggat caaattttg aagaaaatcc aacaaaaggt cactgttaga taccagggca     600
tcaagtgtct cattaaattc ttctgatatg tgaagggatt catcaataga aagacgctta     660
gcatccataa atttctgcct tatgaaatcg atatcagcac taacaacctt gtctgatctg     720
gaagttgtac ttccaatttt agatcttgga ctccggtgca tatttgtttt tgtggcttcc     780
ataccttcaa aaacattaat ggtatctaca ctcctcctgt gtggaatgtc atgcaaacca     840
```

| | |
|---|---|
| gttcgaccat gaaaactact aggtgaagtc tttggtgcat gacttttggt atgtctatgc | 900 |
| ttattatgga ttccagatga gggcaacgaa tcaagaccca tgagccttcc tacagcacct | 960 |
| ggtgaaatat gcctagaatt gacatcattt gaaaattctt c | 1001 |

```
<210> SEQ ID NO 11
<211> LENGTH: 1000
<212> TYPE: DNA
<213> ORGANISM: Zea mays
<220> FEATURE:
<221> NAME/KEY: misc_feature
<222> LOCATION: (500)..(500)
<223> OTHER INFORMATION: N is A, T, C or G

<400> SEQUENCE: 11
```

| | |
|---|---|
| gtgggggagc cacgttttcc agtatttct tggtgactgg accttgacag tttctgcctt | 60 |
| gatgaacaag aatcttcttt tagggactgc aagggcacat tagaatatgg cttccataaa | 120 |
| gaatgtttcc cttccatttg ctcgttgaag atgctctcgg ttcctttctc ttgcggataa | 180 |
| atattgtcca tgtcaataaa ttgatttctt cgagatggct tcaatattgt gatgcagttt | 240 |
| gcggtagagg atggagaacc atgattatgt aggtccctta tgacagcagg atcaaaattt | 300 |
| tgaagaaaat ccaacaaaag gtcactgtta gataccaggg catcaagtgt ctcattaaat | 360 |
| tcttctgata tgtgaaggga ttcatcaata gaaagacgct tagcatccat aaatttctgc | 420 |
| cttatgaaat cgatatcagc actaacaacc ttgtctgatc tggaagttgt acttccaatt | 480 |
| ttagatcttg gactccggtn catatttgtt tttgtggctt ccatacctc aaaaacatta | 540 |
| atggtatcta cactcctcct gtgtggaatg tcatgcaaac cagttcgacc atgaaaacta | 600 |
| ctaggtgaag tctttggtgc atgactttg gtatgtctat gcttattatg gattccagat | 660 |
| gagggcaacg aatcaagacc catgagcctt cctacagcac ctggtgaaat atgcctagaa | 720 |
| ttgacatcat ttgaaaattc ttcttctatc agtatttca ttggtacagc aatggctttt | 780 |
| cttgttttac tttgcctgtc tactgtagca aactgagaag gaaaaaaagg aagaggcaat | 840 |
| agtaacccat tagttggctc ttacaatggc acataagtt gaatgaataa tgaataaaag | 900 |
| tttaatagat gaagatgtaa acgaaataaa gttattccca caaattacca tcaacaaagt | 960 |
| tcgcttgata caatacaaca tacaatttaa aacatttcta | 1000 |

```
<210> SEQ ID NO 12
<211> LENGTH: 948
<212> TYPE: DNA
<213> ORGANISM: Zea mays
<220> FEATURE:
<221> NAME/KEY: misc_feature
<222> LOCATION: (448)..(448)
<223> OTHER INFORMATION: N is A, T, C or G

<400> SEQUENCE: 12
```

| | |
|---|---|
| atattctgtc gacaaaacct tagtacggtc catcagatta catcaagagc gaccctagca | 60 |
| ggtttgggtc ttcgttacct acaaggcagg ttaggcagac ggcagtgaac acgttagcat | 120 |
| gcaacgtttc cgacgtggcg acgtcctttg cctgacgaag cctcgtgctg gcctagacta | 180 |
| gaaggcactg caaagttta gggcatgttg gcctagcttg accctctcc cgagttcttg | 240 |
| atccaccgtg gtgcgcaaac cagtgagtca accctttttt tttgcaggca aacaatccta | 300 |
| gagcagatag tccgaaatgg gacagcgcat catctgatat agatctcgat cttcatccag | 360 |
| acaatggaaa cagaaatgga gcacagcacc actaatccat cagcatcgtc tgacttggca | 420 |
| ccattctatt ctaactccac ccaagaanat tcacatctgg tgacgatgcg atcaagtcaa | 480 |

| | | | |
|---|---|---|---|
| caacattcac | gcgttcgact | agtacaatct gaatgaatca | ggaggctgcc tgacagagga | 540 |
| agaggataac | tgctcctagt | ttacgggggg taaaaaaggg | gaaaaaagtt gagttgttca | 600 |
| gcctgccctg | tcgaacttcc | agtcacaact aacagagcac | acacatcaca gcaggatagt | 660 |
| gtgctcagca | caactaagta | aacactttag caaggctgaa | cactcagcag aacttccagt | 720 |
| gattgttgca | gttcacgcat | gtgacgaacg tcgtcatcgg | ttcatcagca ctccgagtct | 780 |
| gcagctggta | gtaagtcgtc | ttccgctgcc cacatctggc | acacttgaac tggtccgtcg | 840 |
| tcgcctttgg | tgccgctcca | cgctcgcagt cgaacagagc | cttctccttg atctgcatgt | 900 |
| tctcttgctt | ccttgcgtcg | ctagccatct catcaggggg | tatgtctg | 948 |

<210> SEQ ID NO 13
<211> LENGTH: 639
<212> TYPE: DNA
<213> ORGANISM: Zea mays

<400> SEQUENCE: 13

| | | | |
|---|---|---|---|
| atggggaagg | ggttcgcatc | ctacctggcg atgaagacgg | ggccggaggg cggcgacgcg | 60 |
| gcggcggcgc | agcaggctct | gatcgacgcg gacctgcggg | agctcggcgt cgccgcgcgg | 120 |
| aagctcgcca | ccacgcatt | cgtcctcggc ggcgggctgg | ggttcggcac ctccttcctc | 180 |
| aaatggctgg | ccttcctcgc | cgcagtgtat ctcttgatat | tggatcgcac aaattggaag | 240 |
| accaacatgc | tgacagctct | cttggttcct acattttct | tcaccctgcc taatgtgctg | 300 |
| ttttctctga | tcagaggaga | ggtggggaaa tggattgcga | ttattgctgt tattctgcgt | 360 |
| ctattctttc | cacgacactt | cccagattgg ttagagcttc | ctggttccat catcctgctc | 420 |
| acagtggtcg | cccctagcct | gttcgcggac agcttcaggg | agacctcgt tggtgtcttc | 480 |
| atatgccttg | tgatcggatg | ctacctgctc caagaacaca | tcaaggcgtc aggtggattc | 540 |
| aggaacgcct | tcaggaaggg | caatggtgtg tccaactcca | tcggcatcct cctgctcttc | 600 |
| atctaccctg | tctgggccgg | tgtgctgcaa gtcctgtag | | 639 |

<210> SEQ ID NO 14
<211> LENGTH: 1938
<212> TYPE: DNA
<213> ORGANISM: Zea mays

<400> SEQUENCE: 14

| | | | |
|---|---|---|---|
| atggaggtgg | aggctctgga | agaagggg cacgcagctt | tgccaaggc gatgaaatct | 60 |
| ttcggctctt | ccgagcggta | caagcgatcc acgagtggca | gatatttga ggatatgtat | 120 |
| gctacagacg | ctttgcgttc | ttcagacaag acgattgttc | tacctatgcc ggaagtggta | 180 |
| aaagctaagg | tcaaatgtga | tatcactaag gaagctcaac | ccgggagggg agcacaaagc | 240 |
| accttgagaa | aggagattct | tcagctcgag aagcacctca | aggatcaaca ggctgtgcgt | 300 |
| ggtgcgctaa | aaaggcttt | agggcctaac gctggccctg | tcagcttgtc gccagagaat | 360 |
| ccaatgccac | aggcagctaa | tgaattgata cgggagattg | ctacattgga gctggaggtc | 420 |
| aagaacatgg | agcagtatct | cctgacgctg taccggaaag | catttgagca gcagcaagcg | 480 |
| cctgcgtttt | ccccccctga | ccgccgggaa gcttcgaagc | cgtcagtgag ctcgcgttct | 540 |
| gggcagctcc | gggaaacgcc | catggcaacg aagtcttctt | gcaagagtag aggggacgca | 600 |
| gcactgcggt | ccagttaccc | gccagcgcat aagaaactga | acgatccatt ggcggattgc | 660 |
| tgcacatctg | ctcgatttga | tagagtggtt gattcagacg | tcctccgctg ccagtctgcg | 720 |

```
ttgtcatacc gtggagtttg ttcgtccagg atattgcctt cggaggacga tagtcttgca      780
agggctcttc gctcgtgcca ctcgcagcct ttctcattcg tagaggaagg agacaccggt      840
gcatcaggga tgataagctt agcagagtat ctaggaacta atgtagctga ccacatccct      900
gaaactccaa acaacctgtc agaggagatg gtgagatgca tggcggggat atactgcaga      960
ctcgcagatc ctcccttggt tcaccacggc tcgtcctctt caccgtcgtc gtcgttctcc     1020
tcgactagcg caatctctcc gcagtatgtg ggggacatgt ggagtcccaa atacaggaga     1080
gaggcgactc tggactcccg tctgataaac ccgttccatg tcgatggtct gaaggagttc     1140
agtggacctt acaacacaat ggttgaggtt cctatgatta gccgggacag tcggaggctg     1200
aaagaagccg aggacctgct ccagacttac aagttgattt tgtatcggtt ggaagccgtt     1260
gatctgagga gaatgacaga tgaagaaaag atcgcattct gggtcaacat acacaatgct     1320
ttgctgatgc atgcttatct gaagaatggc gtcccacaga acaatctaaa gaaaacatcc     1380
ctacttgtta aggctgcctg caaaatagcc ggacgcaaca tcaacgccgc cgtcatccag     1440
agcattgttc ttgggtgcaa cacacactgc cccgacagtg gctacggac gctgctttac      1500
cccaggatca aaagcaaggt gagcaaagcg ggcatgagt ggcgggcctt tgccgttgcg      1560
caaccggagc ctcttttacg ctttgcgctt tgttccggca gccattctga tcccgcggtg     1620
agggtgtaca ctccgaagcg gctgttccac cagctggagt cggccaagga ggagttcatc     1680
cgggcgacgg ccggcgtgtg gaaggagcag aagctgctgc tccccaagct ggtggaggcg     1740
tacgccaagg acgtgaagct ctcgccgcag ggcctcgtgg acatggtcca gcgctacctc     1800
ccggagagca tgaggatggc cgtgcagcgg tgccagcacg cggcaggtc gtcgggcaag      1860
gtcgtggagt gggtgtccta caacccggcc ttccgctacc tgctcgccag ggacctcgcg     1920
ttccctcacc tcagctga                                                    1938

<210> SEQ ID NO 15
<211> LENGTH: 1272
<212> TYPE: DNA
<213> ORGANISM: Zea mays

<400> SEQUENCE: 15
atggcggcgg tgcttacccg agccggcggc cgctccaagc gatccgtctc cggcttccac       60
ctccgctctg ttctcgcggg gcacgggacc ttctcatctg aagccgcgtc gaccgccgtg      120
ggcgatcgcg tggtcgcggc tacgggcgag cacgatgggg acgacctgcg cagccgcatc      180
ttccgactgg gcctggcgaa gcggagcgcg acggcggcac tcgagaagtg gtccagtgag      240
ggacgcgacg cacccacggc ggagctccgc cgcatcgcgc gcgacctcac ccgcgtccgt      300
cgctacaagc acgcccttga ggtagcgac tggatgaaga cacatcacga gtctgatcta       360
tcagagaacg actacggaat gcgcatcgac ttgattacca aggtcttcgg tgccagtgcc      420
gcggaagatt tctttgagaa gctcccaccg ggagccaaat cgctagaagc ctacacagca     480
cttctgcact cctatggccg gtcgaagatg acggacagag ccgaaaggct gttcgagagg     540
atgaaagacg cgagcctgcc tatggacgcc ctggtctaca cgagatgat gaccctgtac      600
atctccgtgg gggagctcgg taaagtggag gccgtcgcag aggagctgaa acggcagaac      660
gtctctccgg acctgttcac gtacaacctc cgtgccagcg cggccgcggc gtccatggat      720
ctcgagggct tcagagcagt cctcgacgag atgtccagag accgaagtc gtccacagaa      780
ggagggtggg cgctgtaccg ggacctcgcg tccgtgtacg tcgacgcggg ccagcttctg     840
ggctctgtga attcgccgcc ggtggaggcc ggggaggcga ggatcagcca gagggaatgg     900
```

| | | | |
|---|---|---|---|
| atcacctacg | acttcctcgt | catcttgcac | gccggcctcg gcaggccaga gaggataagg | 960 |
| gacatctgga | ggtccatggt | ggcgacctcg | cagtcgcagt cgcagcagca gcagcgcatg | 1020 |
| acgagccgga | actacgtctg | cgtggtctcg | tcctacctgg cgtgcgggcg gctggaggat | 1080 |
| gccggggagg | tcgtcgacca | gtggcagcgc | tctaaggccc ccgagttcga cgtctccgcc | 1140 |
| tgcaaccggc | tgctggacgc | cctcctgcgc | gccggtctcg ccgacgccgc gggtaggttt | 1200 |
| cgggagctga | tgctgcagaa | gcgttgtata | ctgactagca gcagcagcag cagggcggca | 1260 |
| gtggtcgagt | ga | | | 1272 |

<210> SEQ ID NO 16
<211> LENGTH: 1710
<212> TYPE: DNA
<213> ORGANISM: Zea mays

<400> SEQUENCE: 16

| | | | | |
|---|---|---|---|---|
| atggcggagg | ctgtcgcgtc | tgcgggcagg | ctcgccatgg actcttcgac ctccgtctcg | 60 |
| cccggccagg | tttctgctat | tctgggcttt | ctgtgggttt tcgcagcatg ggcgtatgct | 120 |
| gaggttctct | tccataggaa | gaatactgct | tctattaaaa cttttctgct cttcatcttt | 180 |
| gtcagtagac | attcagatgt | caatctagca | gtgatggatg acagttcagt caaagcagaa | 240 |
| gaccagacaa | tgttattgga | ggagggtggt | caagcaatgg ctgcaaagcc agcttatact | 300 |
| tccctcacat | cacaaatact | cagacttata | ttcatggacc agttgcttct tctggagaat | 360 |
| cgtttaacac | tgagggcatt | atctgaattt | ggaggttatc tactttattt ttacatatgt | 420 |
| gatcgtacaa | acttgcttgg | agagtctgcc | aagaattaca gccgagatct gttccttttc | 480 |
| ctctactttc | ttcttatcat | tgtagcagct | atgacttcct ttaaggtcca tcaagacaag | 540 |
| tcatcattca | caggaaaatc | tgtactgtac | ttgaataggc atcaaactga gaatggaag | 600 |
| ggttggatgc | aggtgctatt | cttgatgtac | cattacttca atgctaaaga aatctacaat | 660 |
| gcaatccgtg | tgttcatcgc | tgcatatgtc | tggatgactg gatttggcaa tttctcttat | 720 |
| tattatgtga | ggaaggattt | cagtcttgga | agatttgctc agatgatgtg gcgcctcaat | 780 |
| ttctttgtta | tattctgctg | cattgtcctg | aacaatgatt atacactcta ttatatttgt | 840 |
| cctatgcaca | cccttttcac | cctcatggtt | tatggtgctc ttggaattct aaacaaatac | 900 |
| aacgagatta | gatcagtgat | ggcaatgaaa | tttgttgctt gcttcttggt agttgtcctg | 960 |
| gtttgggaag | ttccaggtgt | ctttgacata | gtatggagcc cattcacatt ccttctaggc | 1020 |
| aagtttcctt | cccaaacctt | tgctatacc | gatccttcta aaccagatct tccccggttg | 1080 |
| catgaatggc | aatttcgatc | tggactggat | cgctacattt ggatcgtggg gatgatatat | 1140 |
| gcatattacc | atccaactgt | tgagaagtgg | ttggagaagc tggaagaaac tgaaatgaga | 1200 |
| accaaactct | atattaagac | ctcaatagtt | acagtgtcaa tgatggctgg ttatttgtgg | 1260 |
| tatgaataca | tttataagct | ggataagatt | acttacaaca agttgcatcc atatacatcc | 1320 |
| tggatccccca | taactgtcta | catatgtcta | cgcaacttca ctcaagaatt cagggcttc | 1380 |
| tccctcacac | tatttgcctg | gcttggaaag | attacactag aaacatacat atctcagttc | 1440 |
| catatctggc | tcagatcaag | tgtgcccaat | ggccaaccaa aatggctatt gtcaataatc | 1500 |
| ccaaattatc | cactgctcaa | tttcatgctg | actactgcta tatatgttgc ggtttcccat | 1560 |
| aggctcttcg | aattgactaa | taccttgaag | atggtatttg taccaaatcg tgacaacaag | 1620 |
| cgcctctcat | acaattttgt | ggcaggaaca | gccatttctg ctgcccctgta ctttgtatcg | 1680 |

```
tttgttctaa ttggcattgc aggatactag                                      1710

<210> SEQ ID NO 17
<211> LENGTH: 675
<212> TYPE: DNA
<213> ORGANISM: Zea mays

<400> SEQUENCE: 17
atggacggcg gcggggtcga tacggccacg acggcggcct ggatggagaa gcaccggcac        60
atgtacgagc gggccacccg gcacccgttc accgtctcca tccgcgacgg taccgtcgac       120
atgtctgcct tcaagcgctg gctgagccag gactatctgt ttgtaaggga atttgttgca       180
ttcatagcaa gtgtactgct caaatgctgc aagcaagaag acagctcgga catggaaatc       240
atcctgggtg gagtagcgtc tatcagcgac gagatctctt ggttcaagaa cgaagctact       300
gtatggggcg tcgatctagc aagtgtttcc cccttaaaag ccaatctaga gtaccacagg       360
tttctccgga gctttactga gccagagatt agctatgctg ttgctgtaac taccttctgg       420
acgatcgaaa ccgtgtacca ggacagcttt ggtttctgca tacaagacgg caacaagacg       480
ccgccggagc tcctgggcac ctgccagaga tggggcagcg ccgggttcag acagtactgc       540
cagtctctgc agagcatcgt ggatcgttgc ttggctaacg caccggctga tgctgtccag       600
agtgctgaag aggccttcgt ccgggtactc gagctggaaa ttggtttctg ggatatgagc       660
tcttctcggt cctaa                                                       675

<210> SEQ ID NO 18
<211> LENGTH: 2991
<212> TYPE: DNA
<213> ORGANISM: Zea mays

<400> SEQUENCE: 18
atgagcatgg caggcattgc gcgcggcaga tcgcgatgga gacagggcga cgggtcgtcg        60
aatcggaatg cggcacactc cactgttcct aacccccgatc accaagaaat tccatgcgat       120
gaaagactat gtagctatgt tgtgttagca gcaggggttg tgtcctctag gaagcaagca       180
acttaccctg gatgctatc tgattcggtg tttgctacag tagacaggca agtaaaaaca       240
agaaaagcca ttgctgtacc aatgaaaata ctgatagaag aagaatttc aaatgatgtc       300 aattctaggc atatttcacc aggtgctgta ggaaggctca tgggtcttga ttcgttgccc       360
tcatctggaa tccataataa gcatagacat accaaaagtc atgcaccaaa gacttcacct       420
agtagttttc atggtcgaac tggtttgcat gacattccac acaggaggag tgtagatacc       480
attaatgttt ttgaaggtat ggaagccaca aaaacaaata tgcaccggag tccaagatct       540
aaaattggaa gtacaacttc cagatcgac aaggttgtta gtgctgatat cgatttcata       600
aggcagaaat ttatggatgc taagcgtctt tctattgatg aatcccttca catatcagaa       660
gaatttaatg agacacttga tgccctggta tctaacagtg acctttttgtt ggattttctt       720 caaaattttg atcctgctgt cataagggac ctacataatc atggttctcc atcctctacc       780
gcaaactgca tcacaatatt gaagccatct cgaagaaatc aattattga catggacaat       840 atttatccgc aagagaaagg aaccgagagc atcttcaacg agcaaatgga agggaaacat       900
tctttatgga agccatattc taatgtgccc ttgcagtccc taaaagaaga ttcttgttca       960
tcaaggcaga aactgtcaag gtccagtcac caagaaaata ctggaaaacg tggctccccc      1020
acccggattt tgtcttgaa gccaaatctt gagaaacctc atgatattga agaagccctt      1080
cccctacatc ataaaatatc ccattctgat tatagaaggc ataaagaatg tccggaggtt      1140
```

```
gatagatgga ctccaaatac tgaagattac atgtgtcagg tgccccttgg agattctgaa    1200
acattaagtc gtatgggaa gggatctaga gaaattgcta gggagatcac caaacagatg    1260
agagctgcta ggggtggaag taggaaacat tctgtcaaac cggagactag aactcttgct    1320
tcagatgaaa ggtcacagtt tcagtcatct gttactagac ccaagactcc agagtcaatt    1380
catagatatt ctgagtcatg tgatgcttgg gcttcttcaa gtctcaactc tttgccaaca    1440
tattcgactg aaacatcaga aagcaaggaa gcaaagaaac acctctctaa cagatggaag    1500
aagacccgtc agtgtcagca tcaagaaact gataatgaca gcttcaacac gcttggggat    1560
atgcttgctc tctctgatca gaatgcatca aatgttgcta cccataaaat gacatgcagg    1620
aaatgtccaa agtcagaagt gcagagtgat agaatacaaa gctcatatcc tcttggcatc    1680
agcaccaatg atggttggaa agacacaact actagtaaat tgacaaggtc caagtctctt    1740
ccaccatcct tcattcgtgg agttcaaaag tcaaacaata gaaaaagaag cggcagcgtt    1800
acatacaatg agttttcaat gcttaaagat gttcttaagg ttggaccccca ctattctgaa    1860 tatgcatatc gtagcaggca aagacgatct ctaagtagag attctacaat tcatggtgat    1920
gaatctgatc cgatgtccac agataatgaa gaaaatatgg tagttgaacg tgagatacat    1980
gtaaattatg aggaaccaat taatggtact gctgtgacat atacatctgg gcagtcacaa    2040
catcctacaa atcttgacca tgaactagat gcaataggtg tactagatac cagttctgca    2100
gtcccttcca gtaataaaaa gtctctttct cctgctgaac aggaccagca agtgcttaag    2160
atgaccacaa cagcactaga taactgcttt cttgtgccta atctcgatga tctgatgcct    2220
aagaatcgcc agcgaactcc aacaaagatg accagcaaag tccaatgtct gttcttgaat    2280
cttccatgga cggagaagat gtttactctg gggattttga gaagatcagt gcagatctcc    2340
aaggcaaagc tcagattgca acttgggctt ctgaagaggg agactacaga cactagagat    2400
ggcagcgagc tttctatatt gagtgatgat gagacagcac gtcgatcact tcctgagact    2460
ggggaatccc atgcttttag gaatacggaa gaaagggact tctcctacgt gttttgatatg    2520 cttgctgctc tgggcatcca cgcggccaac gaggatgacc tccttgacaa ctgctactta    2580
ctggagtgct ctgcaggcct tgatttatac gatgacctcg aacagaagta cgacagcctc    2640
attttatggc ctgtgcatga gaggaagctc ttgtttgata tcacgaatgc tgttcttggg    2700
gacatgatca cctccgtgat gaacggctgc tcgaaggac tgatggcgag gtgctcgcct    2760
ggatggaatc gggaagagtt tgctgagctc gtgtggcaaa gggtggtgca gctccggcaa    2820
gagatagagt tcaaccagga agccctgctg ttgagcgtag agtgggctgg ctctgaagat    2880
ggcgccagtc tggtcgggcg cgatatcggg aatatgttgc aagatgatct cgtacaggaa    2940
attatagctg actttctggg ggcaactaaa tccgccaagc tccgtggcta g              2991
```

<210> SEQ ID NO 19
<211> LENGTH: 1107
<212> TYPE: DNA
<213> ORGANISM: Zea mays

<400> SEQUENCE: 19

```
atggacaggg agcttctaga gacgtttgac gcggccaaga aggcggccga cgaggcggca     60
ggggacggca actcgccgga ggctggccgc tgcctcgacg cgctgcggcg gctgcgcgac    120 attgcgtca acaccgacat cctcgtctcg acgcaggttg gcaaacgcct tcgacccctt    180
actaagcatc ctcactcagg cattcaagca gttgctgcag accttttttgg gtactggaaa    240
```

-continued

```
aaggttgtcc ttgaagagtc aggaaagaaa aatggcggct cagagaatga aagatcaagt    300
gactcttcag gaaaggttga gaaggtgagg cccgtgaaga ttgaaaagaa ctctgcatca    360
gcaagcatga agcttgagaa aagagatgtg gatgttaggg gtcagaagcc taacaatgtc   420
aaagttgaga agactactag taatggttcc aaagctcaat ctgtgaaggt ggaaagggta    480 tccaagaag tcataaggac tcctgactcg aagaggccag catccgtccc caatggccac    540
ccaaagctta catctcttgt caaatgcaat gatcctaccc gagataaaat ccggaaacta    600
cttgctgaag cctttgtaag tgtttccaga gagactagtg atgatgacag agacgaagtg   660
aaaaacatct tggatgaagt cgaggcatgc gacccataca gggttgccgt gacagtagag   720
tctgcactat tcgagaggct tggaccttcc actgggactc acagggcgaa atacaggtca   780
atcatgttca acctgagggc tgaaaacaat accgatttcc ggaggagggt cctcatcggt   840
ctagtggcgc cggagaggct tccagacata cccctgatg agatggctag cgacgcaagg    900
aagcaagaga acatgcagat caaggagaag gctctgttcg actgcgagcg tggagcggca    960
ccaaaggcga cgacggacca gttcaagtgt gccagatgtg ggcagcggaa gacgacttac   1020
taccagctgc agactcggag tgctgatgaa ccgatgacga cgttcgtcac atgcgtgaac   1080
tgcaacaatc actggaagtt ctgctga                                        1107
```

<210> SEQ ID NO 20
<211> LENGTH: 212
<212> TYPE: PRT
<213> ORGANISM: Zea mays

<400> SEQUENCE: 20

```
Met Gly Lys Gly Phe Ala Ser Tyr Leu Ala Met Lys Thr Gly Pro Glu
1               5                  10                  15

Gly Gly Asp Ala Ala Ala Gln Gln Ala Leu Ile Asp Ala Asp Leu
            20                  25                  30

Arg Glu Leu Gly Val Ala Ala Arg Lys Leu Ala Asn His Ala Phe Val
        35                  40                  45

Leu Gly Gly Gly Leu Gly Phe Gly Thr Ser Phe Leu Lys Trp Leu Ala
    50                  55                  60

Phe Leu Ala Ala Val Tyr Leu Leu Ile Leu Asp Arg Thr Asn Trp Lys
65                  70                  75                  80

Thr Asn Met Leu Thr Ala Leu Leu Val Pro Tyr Ile Phe Phe Thr Leu
                85                  90                  95

Pro Asn Val Leu Phe Ser Leu Ile Arg Gly Glu Val Gly Lys Trp Ile
            100                 105                 110

Ala Ile Ile Ala Val Ile Leu Arg Leu Phe Phe Pro Arg His Phe Pro
        115                 120                 125

Asp Trp Leu Glu Leu Pro Gly Ser Ile Ile Leu Thr Val Val Ala
    130                 135                 140

Pro Ser Leu Phe Ala Asp Ser Phe Arg Gly Asp Leu Val Gly Val Phe
145                 150                 155                 160

Ile Cys Leu Val Ile Gly Cys Tyr Leu Leu Gln Glu His Ile Lys Ala
                165                 170                 175

Ser Gly Gly Phe Arg Asn Ala Phe Arg Lys Gly Asn Gly Val Ser Asn
            180                 185                 190

Ser Ile Gly Ile Leu Leu Leu Phe Ile Tyr Pro Val Trp Ala Gly Val
        195                 200                 205

Leu Gln Val Leu
    210
```

```
<210> SEQ ID NO 21
<211> LENGTH: 645
<212> TYPE: PRT
<213> ORGANISM: Zea mays

<400> SEQUENCE: 21

Met Glu Val Glu Ala Leu Glu Lys Lys Gly His Ala Ala Phe Ala Lys
1               5                   10                  15

Ala Met Lys Ser Phe Gly Ser Ser Glu Arg Tyr Lys Arg Ser Thr Ser
            20                  25                  30

Gly Arg Tyr Phe Glu Asp Met Tyr Ala Thr Asp Ala Leu Arg Ser Ser
        35                  40                  45

Asp Lys Thr Ile Val Leu Pro Met Pro Glu Val Val Lys Ala Lys Val
    50                  55                  60

Lys Cys Asp Ile Thr Lys Glu Ala Gln Pro Gly Arg Gly Ala Gln Ser
65                  70                  75                  80

Thr Leu Arg Lys Glu Ile Leu Gln Leu Glu Lys His Leu Lys Asp Gln
                85                  90                  95

Gln Ala Val Arg Gly Ala Leu Glu Lys Ala Leu Gly Pro Asn Ala Gly
            100                 105                 110

Pro Val Ser Leu Ser Pro Glu Asn Pro Met Pro Gln Ala Ala Asn Glu
        115                 120                 125

Leu Ile Arg Glu Ile Ala Thr Leu Glu Leu Glu Val Lys Asn Met Glu
    130                 135                 140

Gln Tyr Leu Leu Thr Leu Tyr Arg Lys Ala Phe Glu Gln Gln Gln Ala
145                 150                 155                 160

Pro Ala Phe Ser Pro Pro Asp Arg Arg Glu Ala Ser Lys Pro Ser Val
                165                 170                 175

Ser Ser Arg Ser Gly Gln Leu Arg Glu Thr Pro Met Ala Thr Lys Ser
            180                 185                 190

Ser Cys Lys Ser Arg Gly Asp Ala Ala Leu Arg Ser Ser Tyr Pro Pro
        195                 200                 205

Ala His Lys Lys Leu Asn Asp Pro Leu Ala Asp Cys Cys Thr Ser Ala
    210                 215                 220

Arg Phe Asp Arg Val Val Asp Ser Asp Val Leu Arg Cys Gln Ser Ala
225                 230                 235                 240

Leu Ser Tyr Arg Gly Val Cys Ser Ser Arg Ile Leu Pro Ser Glu Asp
                245                 250                 255

Asp Ser Leu Ala Arg Ala Leu Arg Ser Cys His Ser Gln Pro Phe Ser
            260                 265                 270

Phe Val Glu Glu Gly Asp Thr Gly Ala Ser Gly Met Ile Ser Leu Ala
        275                 280                 285

Glu Tyr Leu Gly Thr Asn Val Ala Asp His Ile Pro Glu Thr Pro Asn
    290                 295                 300

Asn Leu Ser Glu Glu Met Val Arg Cys Met Ala Gly Ile Tyr Cys Arg
305                 310                 315                 320

Leu Ala Asp Pro Pro Leu Val His His Gly Ser Ser Ser Pro Ser
                325                 330                 335

Ser Ser Phe Ser Ser Thr Ser Ala Ile Ser Pro Gln Tyr Val Gly Asp
            340                 345                 350

Met Trp Ser Pro Lys Tyr Arg Arg Glu Ala Thr Leu Asp Ser Arg Leu
        355                 360                 365

Ile Asn Pro Phe His Val Asp Gly Leu Lys Glu Phe Ser Gly Pro Tyr
```

```
                370             375             380
Asn Thr Met Val Glu Val Pro Met Ile Ser Arg Asp Ser Arg Leu
385             390             395             400

Lys Glu Ala Glu Asp Leu Leu Gln Thr Tyr Lys Leu Ile Leu Tyr Arg
            405             410             415

Leu Glu Ala Val Asp Leu Arg Arg Met Thr Asp Glu Glu Lys Ile Ala
            420             425             430

Phe Trp Val Asn Ile His Asn Ala Leu Leu Met His Ala Tyr Leu Lys
            435             440             445

Asn Gly Val Pro Gln Asn Asn Leu Lys Lys Thr Ser Leu Leu Val Lys
            450             455             460

Ala Ala Cys Lys Ile Ala Gly Arg Asn Ile Asn Ala Ala Val Ile Gln
465             470             475             480

Ser Ile Val Leu Gly Cys Asn Thr His Cys Pro Gly Gln Trp Leu Arg
                485             490             495

Thr Leu Leu Tyr Pro Arg Ile Lys Ser Lys Val Ser Lys Ala Gly His
                500             505             510

Glu Trp Arg Ala Phe Ala Val Ala Gln Pro Glu Pro Leu Leu Arg Phe
            515             520             525

Ala Leu Cys Ser Gly Ser His Ser Asp Pro Ala Val Arg Val Tyr Thr
530             535             540

Pro Lys Arg Leu Phe His Gln Leu Glu Ser Ala Lys Glu Glu Phe Ile
545             550             555             560

Arg Ala Thr Ala Gly Val Trp Lys Glu Gln Lys Leu Leu Pro Lys
            565             570             575

Leu Val Glu Ala Tyr Ala Lys Asp Val Lys Leu Ser Pro Gln Gly Leu
            580             585             590

Val Asp Met Val Gln Arg Tyr Leu Pro Glu Ser Met Arg Met Ala Val
            595             600             605

Gln Arg Cys Gln His Gly Gly Arg Ser Ser Gly Lys Val Val Glu Trp
            610             615             620

Val Ser Tyr Asn Pro Ala Phe Arg Tyr Leu Leu Ala Arg Asp Leu Ala
625             630             635             640

Phe Pro His Leu Ser
            645

<210> SEQ ID NO 22
<211> LENGTH: 423
<212> TYPE: PRT
<213> ORGANISM: Zea mays

<400> SEQUENCE: 22

Met Ala Ala Val Leu Thr Arg Ala Gly Gly Arg Ser Lys Arg Ser Val
1               5               10              15

Ser Gly Phe His Leu Arg Ser Val Leu Ala Gly His Gly Thr Phe Ser
            20              25              30

Ser Glu Ala Ala Ser Thr Ala Val Gly Asp Arg Val Ala Ala Thr
            35              40              45

Gly Glu His Asp Gly Asp Leu Arg Ser Arg Ile Phe Arg Leu Gly
        50              55              60

Leu Ala Lys Arg Ser Ala Thr Ala Ala Leu Glu Lys Trp Ser Ser Glu
65              70              75              80

Gly Arg Asp Ala Pro Thr Ala Glu Leu Arg Arg Ile Ala Arg Asp Leu
            85              90              95
```

```
Thr Arg Val Arg Arg Tyr Lys His Ala Leu Glu Val Ala Asp Trp Met
            100                 105                 110

Lys Thr His His Glu Ser Asp Leu Ser Glu Asn Asp Tyr Gly Met Arg
        115                 120                 125

Ile Asp Leu Ile Thr Lys Val Phe Gly Ala Ser Ala Ala Glu Asp Phe
    130                 135                 140

Phe Glu Lys Leu Pro Pro Gly Ala Lys Ser Leu Glu Ala Tyr Thr Ala
145                 150                 155                 160

Leu Leu His Ser Tyr Gly Arg Ser Lys Met Thr Asp Arg Ala Glu Arg
                165                 170                 175

Leu Phe Glu Arg Met Lys Asp Ala Ser Leu Pro Met Asp Ala Leu Val
            180                 185                 190

Tyr Asn Glu Met Met Thr Leu Tyr Ile Ser Val Gly Glu Leu Gly Lys
        195                 200                 205

Val Glu Ala Val Ala Glu Glu Leu Lys Arg Gln Asn Val Ser Pro Asp
    210                 215                 220

Leu Phe Thr Tyr Asn Leu Arg Ala Ser Ala Ala Ala Ser Met Asp
225                 230                 235                 240

Leu Glu Gly Phe Arg Ala Val Leu Asp Glu Met Ser Arg Asp Pro Lys
                245                 250                 255

Ser Ser Thr Glu Gly Gly Trp Ala Leu Tyr Arg Asp Leu Ala Ser Val
            260                 265                 270

Tyr Val Asp Ala Gly Gln Leu Leu Gly Ser Val Asn Ser Pro Pro Val
        275                 280                 285

Glu Ala Gly Glu Ala Arg Ile Ser Gln Arg Glu Trp Ile Thr Tyr Asp
    290                 295                 300

Phe Leu Val Ile Leu His Ala Gly Leu Gly Arg Pro Glu Arg Ile Arg
305                 310                 315                 320

Asp Ile Trp Arg Ser Met Val Ala Thr Ser Gln Ser Gln Ser Gln Gln
                325                 330                 335

Gln Gln Arg Met Thr Ser Arg Asn Tyr Val Cys Val Val Ser Ser Tyr
            340                 345                 350

Leu Ala Cys Gly Arg Leu Glu Asp Ala Gly Glu Val Val Asp Gln Trp
        355                 360                 365

Gln Arg Ser Lys Ala Pro Glu Phe Asp Val Ser Ala Cys Asn Arg Leu
    370                 375                 380

Leu Asp Ala Leu Leu Arg Ala Gly Leu Ala Asp Ala Gly Arg Phe
385                 390                 395                 400

Arg Glu Leu Met Leu Gln Lys Arg Cys Ile Leu Thr Ser Ser Ser Ser
                405                 410                 415

Ser Arg Ala Ala Val Val Glu
            420

<210> SEQ ID NO 23
<211> LENGTH: 569
<212> TYPE: PRT
<213> ORGANISM: Zea mays

<400> SEQUENCE: 23

Met Ala Glu Ala Val Ala Ser Ala Gly Arg Leu Ala Met Asp Ser Ser
1               5                   10                  15

Thr Ser Val Ser Pro Gly Gln Val Ser Ala Ile Leu Gly Phe Leu Trp
            20                  25                  30

Val Phe Ala Ala Trp Ala Tyr Ala Glu Val Leu Phe His Arg Lys Asn
        35                  40                  45
```

-continued

```
Thr Ala Ser Ile Lys Thr Phe Trp Leu Phe Ile Phe Val Ser Arg His
    50                  55                  60
Ser Asp Val Asn Leu Ala Val Met Asp Asp Ser Val Lys Ala Glu
65                  70                  75                  80
Asp Gln Thr Met Leu Leu Glu Glu Gly Gln Ala Met Ala Ala Lys
                85                  90                  95
Pro Ala Tyr Thr Ser Leu Thr Ser Gln Ile Leu Arg Leu Ile Phe Met
            100                 105                 110
Asp Gln Leu Leu Leu Leu Glu Asn Arg Leu Thr Leu Arg Ala Leu Ser
        115                 120                 125
Glu Phe Gly Gly Tyr Leu Leu Tyr Phe Tyr Ile Cys Asp Arg Thr Asn
    130                 135                 140
Leu Leu Gly Glu Ser Ala Lys Asn Tyr Ser Arg Asp Leu Phe Leu Phe
145                 150                 155                 160
Leu Tyr Phe Leu Leu Ile Ile Val Ala Ala Met Thr Ser Phe Lys Val
                165                 170                 175
His Gln Asp Lys Ser Ser Phe Thr Gly Lys Ser Val Leu Tyr Leu Asn
            180                 185                 190
Arg His Gln Thr Glu Glu Trp Lys Gly Trp Met Gln Val Leu Phe Leu
        195                 200                 205
Met Tyr His Tyr Phe Asn Ala Lys Glu Ile Tyr Asn Ala Ile Arg Val
    210                 215                 220
Phe Ile Ala Ala Tyr Val Trp Met Thr Gly Phe Gly Asn Phe Ser Tyr
225                 230                 235                 240
Tyr Tyr Val Arg Lys Asp Phe Ser Leu Gly Arg Phe Ala Gln Met Met
                245                 250                 255
Trp Arg Leu Asn Phe Phe Val Ile Phe Cys Cys Ile Val Leu Asn Asn
            260                 265                 270
Asp Tyr Thr Leu Tyr Tyr Ile Cys Pro Met His Thr Leu Phe Thr Leu
        275                 280                 285
Met Val Tyr Gly Ala Leu Gly Ile Leu Asn Lys Tyr Asn Glu Ile Arg
    290                 295                 300
Ser Val Met Ala Met Lys Phe Val Ala Cys Phe Leu Val Val Val Leu
305                 310                 315                 320
Val Trp Glu Val Pro Gly Val Phe Asp Ile Val Trp Ser Pro Phe Thr
                325                 330                 335
Phe Leu Leu Gly Lys Phe Pro Ser Gln Thr Phe Cys Tyr Thr Asp Pro
            340                 345                 350
Ser Lys Pro Asp Leu Pro Arg Leu His Glu Trp Gln Phe Arg Ser Gly
        355                 360                 365
Leu Asp Arg Tyr Ile Trp Ile Val Gly Met Ile Tyr Ala Tyr His His
    370                 375                 380
Pro Thr Val Glu Lys Trp Leu Glu Lys Leu Glu Glu Thr Glu Met Arg
385                 390                 395                 400
Thr Lys Leu Tyr Ile Lys Thr Ser Ile Val Thr Val Ser Met Met Ala
                405                 410                 415
Gly Tyr Leu Trp Tyr Glu Tyr Ile Tyr Lys Leu Asp Lys Ile Thr Tyr
            420                 425                 430
Asn Lys Leu His Pro Tyr Thr Ser Trp Ile Pro Ile Thr Val Tyr Ile
        435                 440                 445
Cys Leu Arg Asn Phe Thr Gln Glu Phe Arg Gly Phe Ser Leu Thr Leu
    450                 455                 460
```

```
Phe Ala Trp Leu Gly Lys Ile Thr Leu Glu Thr Tyr Ile Ser Gln Phe
465                 470                 475                 480

His Ile Trp Leu Arg Ser Ser Val Pro Asn Gly Gln Pro Lys Trp Leu
            485                 490                 495

Leu Ser Ile Ile Pro Asn Tyr Pro Leu Leu Asn Phe Met Leu Thr Thr
            500                 505                 510

Ala Ile Tyr Val Ala Val Ser His Arg Leu Phe Glu Leu Thr Asn Thr
        515                 520                 525

Leu Lys Met Val Phe Val Pro Asn Arg Asp Asn Lys Arg Leu Ser Tyr
    530                 535                 540

Asn Phe Val Ala Gly Thr Ala Ile Ser Ala Ala Leu Tyr Phe Val Ser
545                 550                 555                 560

Phe Val Leu Ile Gly Ile Ala Gly Tyr
                565
```

<210> SEQ ID NO 24
<211> LENGTH: 224
<212> TYPE: PRT
<213> ORGANISM: Zea mays

<400> SEQUENCE: 24

```
Met Asp Gly Gly Gly Val Asp Thr Ala Thr Ala Ala Trp Met Glu
1               5                   10                  15

Lys His Arg His Met Tyr Glu Arg Ala Thr Arg His Pro Phe Thr Val
                20                  25                  30

Ser Ile Arg Asp Gly Thr Val Asp Met Ser Ala Phe Lys Arg Trp Leu
            35                  40                  45

Ser Gln Asp Tyr Leu Phe Val Arg Glu Phe Val Ala Phe Ile Ala Ser
50                  55                  60

Val Leu Leu Lys Cys Cys Lys Gln Glu Asp Ser Ser Asp Met Glu Ile
65                  70                  75                  80

Ile Leu Gly Gly Val Ala Ser Ile Ser Asp Glu Ile Ser Trp Phe Lys
                85                  90                  95

Asn Glu Ala Thr Val Trp Gly Val Asp Leu Ala Ser Val Ser Pro Leu
            100                 105                 110

Lys Ala Asn Leu Glu Tyr His Arg Phe Leu Arg Ser Phe Thr Glu Pro
        115                 120                 125

Glu Ile Ser Tyr Ala Val Ala Val Thr Thr Phe Trp Thr Ile Glu Thr
130                 135                 140

Val Tyr Gln Asp Ser Phe Gly Phe Cys Ile Gln Asp Gly Asn Lys Thr
145                 150                 155                 160

Pro Pro Glu Leu Leu Gly Thr Cys Gln Arg Trp Gly Ser Ala Gly Phe
                165                 170                 175

Arg Gln Tyr Cys Gln Ser Leu Gln Ser Ile Val Asp Arg Cys Leu Ala
            180                 185                 190

Asn Ala Pro Ala Asp Ala Val Gln Ser Ala Glu Glu Ala Phe Val Arg
        195                 200                 205

Val Leu Glu Leu Glu Ile Gly Phe Trp Asp Met Ser Ser Ser Arg Ser
210                 215                 220
```

<210> SEQ ID NO 25
<211> LENGTH: 996
<212> TYPE: PRT
<213> ORGANISM: Zea mays

<400> SEQUENCE: 25

```
Met Ser Met Ala Gly Ile Ala Arg Gly Arg Ser Arg Trp Arg Gln Gly
1               5                   10                  15

Asp Gly Ser Ser Asn Arg Asn Ala Ala His Ser Thr Val Pro Asn Pro
            20                  25                  30

Asp His Gln Glu Ile Pro Cys Asp Glu Arg Leu Cys Ser Tyr Val Val
            35                  40                  45

Leu Ala Ala Gly Val Val Ser Ser Arg Lys Gln Ala Thr Tyr Pro Gly
    50                  55                  60

Met Leu Ser Asp Ser Val Phe Ala Thr Val Asp Arg Gln Ser Lys Thr
65                  70                  75                  80

Arg Lys Ala Ile Ala Val Pro Met Lys Ile Leu Ile Glu Glu Glu Phe
                85                  90                  95

Ser Asn Asp Val Asn Ser Arg His Ile Ser Pro Gly Ala Val Gly Arg
            100                 105                 110

Leu Met Gly Leu Asp Ser Leu Pro Ser Ser Gly Ile His Asn Lys His
        115                 120                 125

Arg His Thr Lys Ser His Ala Pro Lys Thr Ser Pro Ser Ser Phe His
    130                 135                 140

Gly Arg Thr Gly Leu His Asp Ile Pro His Arg Arg Ser Val Asp Thr
145                 150                 155                 160

Ile Asn Val Phe Glu Gly Met Glu Ala Thr Lys Thr Asn Met His Arg
                165                 170                 175

Ser Pro Arg Ser Lys Ile Gly Ser Thr Thr Ser Arg Ser Asp Lys Val
            180                 185                 190

Val Ser Ala Asp Ile Asp Phe Ile Arg Gln Lys Phe Met Asp Ala Lys
        195                 200                 205

Arg Leu Ser Ile Asp Glu Ser Leu His Ile Ser Glu Glu Phe Asn Glu
    210                 215                 220

Thr Leu Asp Ala Leu Val Ser Asn Ser Asp Leu Leu Leu Asp Phe Leu
225                 230                 235                 240

Gln Asn Phe Asp Pro Ala Val Ile Arg Asp Leu His Asn His Gly Ser
                245                 250                 255

Pro Ser Ser Thr Ala Asn Cys Ile Thr Ile Leu Lys Pro Ser Arg Arg
            260                 265                 270

Asn Gln Phe Ile Asp Met Asp Asn Ile Tyr Pro Gln Glu Lys Gly Thr
        275                 280                 285

Glu Ser Ile Phe Asn Glu Gln Met Glu Gly Lys His Ser Leu Trp Lys
    290                 295                 300

Pro Tyr Ser Asn Val Pro Leu Gln Ser Leu Lys Glu Asp Ser Cys Ser
305                 310                 315                 320

Ser Arg Gln Lys Leu Ser Arg Ser Ser His Gln Glu Asn Thr Gly Lys
                325                 330                 335

Arg Gly Ser Pro Thr Arg Ile Val Val Leu Lys Pro Asn Leu Glu Lys
            340                 345                 350

Pro His Asp Ile Glu Glu Ala Leu Pro Leu His His Lys Ile Ser His
        355                 360                 365

Ser Asp Tyr Arg Arg His Lys Glu Cys Pro Glu Val Asp Arg Trp Thr
    370                 375                 380

Pro Asn Thr Glu Asp Tyr Met Cys Gln Val Pro Leu Gly Asp Ser Glu
385                 390                 395                 400

Thr Leu Ser Arg Met Gly Lys Gly Ser Arg Glu Ile Ala Arg Glu Ile
                405                 410                 415

Thr Lys Gln Met Arg Ala Ala Arg Gly Gly Ser Arg Lys His Ser Val
```

-continued

```
                420             425             430
Lys Pro Glu Thr Arg Thr Leu Ala Ser Asp Glu Arg Ser Gln Phe Gln
            435             440             445
Ser Ser Val Thr Arg Pro Lys Thr Pro Glu Ser Ile His Arg Tyr Ser
450             455             460
Glu Ser Cys Asp Ala Trp Ala Ser Ser Leu Asn Ser Leu Pro Thr
465             470             475             480
Tyr Ser Thr Glu Thr Ser Glu Ser Lys Glu Ala Lys Lys His Leu Ser
            485             490             495
Asn Arg Trp Lys Lys Thr Arg Gln Cys Gln His Gln Glu Thr Asp Asn
            500             505             510
Asp Ser Phe Asn Thr Leu Gly Asp Met Leu Ala Leu Ser Asp Gln Asn
            515             520             525
Ala Ser Asn Val Ala Thr His Lys Met Thr Cys Arg Lys Cys Pro Lys
            530             535             540
Ser Glu Val Gln Ser Asp Arg Ile Gln Ser Ser Tyr Pro Leu Gly Ile
545             550             555             560
Ser Thr Asn Asp Gly Trp Lys Asp Thr Thr Thr Ser Lys Leu Thr Arg
            565             570             575
Ser Lys Ser Leu Pro Pro Ser Phe Ile Arg Gly Val Gln Lys Ser Asn
            580             585             590
Asn Arg Lys Arg Ser Gly Ser Val Thr Tyr Asn Glu Phe Ser Met Leu
            595             600             605
Lys Asp Val Leu Lys Val Gly Pro His Tyr Ser Glu Tyr Ala Tyr Arg
            610             615             620
Ser Arg Gln Arg Arg Ser Leu Ser Arg Asp Ser Thr Ile His Gly Asp
625             630             635             640
Glu Ser Asp Pro Met Ser Thr Asp Asn Glu Asn Met Val Val Glu
            645             650             655
Arg Glu Ile His Val Asn Tyr Glu Glu Pro Ile Asn Gly Thr Ala Val
            660             665             670
Thr Tyr Thr Ser Gly Gln Ser Gln His Pro Thr Asn Leu Asp His Glu
            675             680             685
Leu Asp Ala Ile Gly Val Leu Asp Thr Ser Ser Ala Val Pro Phe Ser
            690             695             700
Asn Lys Lys Ser Leu Ser Pro Ala Glu Gln Asp Gln Gln Val Leu Lys
705             710             715             720
Met Thr Thr Thr Ala Leu Asp Asn Cys Phe Leu Val Pro Asn Leu Asp
            725             730             735
Asp Leu Met Pro Lys Asn Arg Gln Arg Thr Pro Thr Lys Met Thr Ser
            740             745             750
Lys Val Gln Cys Leu Phe Leu Asn Leu Pro Trp Thr Glu Lys Met Phe
            755             760             765
Thr Leu Gly Ile Leu Arg Arg Ser Val Gln Ile Ser Lys Ala Lys Leu
            770             775             780
Arg Leu Gln Leu Gly Leu Leu Lys Arg Glu Thr Thr Asp Thr Arg Asp
785             790             795             800
Gly Ser Glu Leu Ser Ile Leu Ser Asp Asp Glu Thr Ala Arg Arg Ser
            805             810             815
Leu Pro Glu Thr Gly Glu Ser His Ala Phe Arg Asn Thr Glu Glu Arg
            820             825             830
Asp Phe Ser Tyr Val Phe Asp Met Leu Ala Ala Leu Gly Ile His Ala
            835             840             845
```

```
Ala Asn Glu Asp Asp Leu Leu Asp Asn Cys Tyr Leu Leu Glu Cys Ser
            850                 855                 860

Ala Gly Leu Asp Leu Tyr Asp Asp Leu Glu Gln Lys Tyr Asp Ser Leu
865                 870                 875                 880

Ile Leu Trp Pro Val His Glu Arg Lys Leu Leu Phe Asp Ile Thr Asn
                    885                 890                 895

Ala Val Leu Gly Asp Met Ile Thr Ser Val Met Asn Gly Cys Ser Lys
                900                 905                 910

Gly Leu Met Ala Arg Cys Ser Pro Gly Trp Asn Arg Glu Glu Phe Ala
            915                 920                 925

Glu Leu Val Trp Gln Arg Val Val Gln Leu Arg Gln Glu Ile Glu Phe
            930                 935                 940

Asn Gln Glu Ala Leu Leu Leu Ser Val Glu Trp Ala Gly Ser Glu Asp
945                 950                 955                 960

Gly Ala Ser Leu Val Gly Arg Asp Ile Gly Asn Met Leu Gln Asp Asp
                965                 970                 975

Leu Val Gln Glu Ile Ile Ala Asp Phe Leu Gly Ala Thr Lys Ser Ala
            980                 985                 990

Lys Leu Arg Gly
            995

<210> SEQ ID NO 26
<211> LENGTH: 368
<212> TYPE: PRT
<213> ORGANISM: Zea mays

<400> SEQUENCE: 26

Met Asp Arg Glu Leu Leu Glu Thr Phe Asp Ala Ala Lys Lys Ala Ala
1               5                   10                  15

Asp Glu Ala Ala Gly Asp Gly Asn Ser Pro Glu Ala Gly Arg Cys Leu
                20                  25                  30

Asp Ala Leu Arg Arg Leu Arg Asp Ile Arg Val Asn Thr Asp Ile Leu
            35                  40                  45

Val Ser Thr Gln Val Gly Lys Arg Leu Arg Pro Leu Thr Lys His Pro
50                  55                  60

His Ser Gly Ile Gln Ala Val Ala Ala Asp Leu Phe Gly Tyr Trp Lys
65                  70                  75                  80

Lys Val Val Leu Glu Glu Ser Gly Lys Lys Asn Gly Gly Ser Glu Asn
                85                  90                  95

Glu Arg Ser Ser Asp Ser Ser Gly Lys Val Glu Lys Val Arg Pro Val
            100                 105                 110

Lys Ile Glu Lys Asn Ser Ala Ser Ala Ser Met Lys Leu Glu Lys Arg
            115                 120                 125

Asp Val Asp Val Arg Gly Gln Lys Pro Asn Asn Val Lys Val Glu Lys
130                 135                 140

Thr Thr Ser Asn Gly Ser Lys Ala Gln Ser Val Lys Val Glu Arg Val
145                 150                 155                 160

Ser Lys Glu Val Ile Arg Thr Pro Asp Ser Lys Arg Pro Ala Ser Val
                165                 170                 175

Pro Asn Gly His Pro Lys Leu Thr Ser Leu Val Lys Cys Asn Asp Pro
            180                 185                 190

Thr Arg Asp Lys Ile Arg Glu Leu Leu Ala Glu Ala Phe Val Ser Val
            195                 200                 205

Ser Arg Glu Thr Ser Asp Asp Asp Arg Asp Glu Val Lys Asn Ile Leu
```

```
            210                 215                 220
Asp Glu Val Glu Ala Cys Asp Pro Tyr Arg Val Ala Thr Val Glu
225                 230                 235                 240

Ser Ala Leu Phe Glu Arg Leu Gly Pro Ser Thr Gly Thr His Arg Ala
                245                 250                 255

Lys Tyr Arg Ser Ile Met Phe Asn Leu Arg Ala Glu Asn Asn Thr Asp
            260                 265                 270

Phe Arg Arg Arg Val Leu Ile Gly Leu Val Ala Pro Glu Arg Leu Pro
        275                 280                 285

Asp Ile Pro Pro Asp Glu Met Ala Ser Asp Ala Arg Lys Gln Glu Asn
    290                 295                 300

Met Gln Ile Lys Glu Lys Ala Leu Phe Asp Cys Glu Arg Gly Ala Ala
305                 310                 315                 320

Pro Lys Ala Thr Thr Asp Gln Phe Lys Cys Ala Arg Cys Gly Gln Arg
                325                 330                 335

Lys Thr Thr Tyr Tyr Gln Leu Gln Thr Arg Ser Ala Asp Glu Pro Met
            340                 345                 350

Thr Thr Phe Val Thr Cys Val Asn Cys Asn Asn His Trp Lys Phe Cys
        355                 360                 365

<210> SEQ ID NO 27
<211> LENGTH: 19
<212> TYPE: DNA
<213> ORGANISM: Artificial Sequence
<220> FEATURE:
<223> OTHER INFORMATION: Probe

<400> SEQUENCE: 27
tgtgaatcga aatcgatct                                        19

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tcacaatggg cagaagcata                                       20

<210> SEQ ID NO 29
<211> LENGTH: 19
<212> TYPE: DNA
<213> ORGANISM: Artificial Sequence
<220> FEATURE:
<223> OTHER INFORMATION: Probe

<400> SEQUENCE: 29
tgtgaatcga attcgatct                                        19

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
aaccaacatg caagtcctac att                                   23

<210> SEQ ID NO 31
```

```
<211> LENGTH: 19
<212> TYPE: DNA
<213> ORGANISM: Artificial Sequence
<220> FEATURE:
<223> OTHER INFORMATION: Probe

<400> SEQUENCE: 31
acattgtttc atcctgtgc                                                    19

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tcatcctttt gcttggtgac tct                                               23

<210> SEQ ID NO 33
<211> LENGTH: 19
<212> TYPE: DNA
<213> ORGANISM: Artificial Sequence
<220> FEATURE:
<223> OTHER INFORMATION: Probe

<400> SEQUENCE: 33
aacattgttt cgtcctgtg                                                    19

<210> SEQ ID NO 34
<211> LENGTH: 20
<212> TYPE: DNA
<213> ORGANISM: Artificial Sequence
<220> FEATURE:
<223> OTHER INFORMATION: Probe

<400> SEQUENCE: 34
cctgacgcct tgatgtgttc                                                   20

<210> SEQ ID NO 35
<211> LENGTH: 23
<212> TYPE: DNA
<213> ORGANISM: Artificial Sequence
<220> FEATURE:
<223> OTHER INFORMATION: Probe

<400> SEQUENCE: 35
agagctaaga gtcaatgaag aac                                               23

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
cttctccaga gcctccacct                                                   20

<210> SEQ ID NO 37
<211> LENGTH: 22
<212> TYPE: DNA
<213> ORGANISM: Artificial Sequence
<220> FEATURE:
<223> OTHER INFORMATION: Probe

<400> SEQUENCE: 37
```
agctaagagt caatcaagaa ct    22

<210> SEQ ID NO 38
<211> LENGTH: 21
<212> TYPE: DNA
<213> ORGANISM: Artificial Sequence
<220> FEATURE:
<223> OTHER INFORMATION: Primer

<400> SEQUENCE: 38
tgggcaacta cagctgatct c    21

<210> SEQ ID NO 39
<211> LENGTH: 18
<212> TYPE: DNA
<213> ORGANISM: Artificial Sequence
<220> FEATURE:
<223> OTHER INFORMATION: Probe

<400> SEQUENCE: 39
agcacactga ggaactgt    18

<210> SEQ ID NO 40
<211> LENGTH: 19
<212> TYPE: DNA
<213> ORGANISM: Artificial Sequence
<220> FEATURE:
<223> OTHER INFORMATION: Primer

<400> SEQUENCE: 40
acatagtgcc aggctcgtg    19

<210> SEQ ID NO 41
<211> LENGTH: 16
<212> TYPE: DNA
<213> ORGANISM: Artificial Sequence
<220> FEATURE:
<223> OTHER INFORMATION: Probe

<400> SEQUENCE: 41
aagcagagca ccccat    16

<210> SEQ ID NO 42
<211> LENGTH: 24
<212> TYPE: DNA
<213> ORGANISM: Artificial Sequence
<220> FEATURE:
<223> OTHER INFORMATION: Primer

<400> SEQUENCE: 42
agggtagtta gggccaggaa gaag    24

<210> SEQ ID NO 43
<211> LENGTH: 21
<212> TYPE: DNA
<213> ORGANISM: Artificial Sequence
<220> FEATURE:
<223> OTHER INFORMATION: Probe

<400> SEQUENCE: 43
aacactttaa tccactaacc t    21

<210> SEQ ID NO 44
<211> LENGTH: 18
<212> TYPE: DNA

```
<213> ORGANISM: Artificial Sequence
<220> FEATURE:
<223> OTHER INFORMATION: Primer

<400> SEQUENCE: 44
aattacagcc gagatctg                                                    18

<210> SEQ ID NO 45
<211> LENGTH: 17
<212> TYPE: DNA
<213> ORGANISM: Artificial Sequence
<220> FEATURE:
<223> OTHER INFORMATION: Probe

<400> SEQUENCE: 45
acagccgaga tatgttc                                                     17

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gctgctacaa tgataagaag                                                  20

<210> SEQ ID NO 47
<211> LENGTH: 22
<212> TYPE: DNA
<213> ORGANISM: Artificial Sequence
<220> FEATURE:
<223> OTHER INFORMATION: Primer

<400> SEQUENCE: 47
tgaagtggct aagctttgac ct                                               22

<210> SEQ ID NO 48
<211> LENGTH: 21
<212> TYPE: DNA
<213> ORGANISM: Artificial Sequence
<220> FEATURE:
<223> OTHER INFORMATION: Probe

<400> SEQUENCE: 48
acatcaatct aattactacc a                                                21

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
ctgtacatca atctaaatac tac                                              23

<210> SEQ ID NO 50
<211> LENGTH: 23
<212> TYPE: DNA
<213> ORGANISM: Artificial Sequence
<220> FEATURE:
<223> OTHER INFORMATION: Probe

<400> SEQUENCE: 50
ttctcccaga aacacctctg act                                              23
```

```
<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
aacctgtggt actctagatt ggct                                          24

<210> SEQ ID NO 52
<211> LENGTH: 17
<212> TYPE: DNA
<213> ORGANISM: Artificial Sequence
<220> FEATURE:
<223> OTHER INFORMATION: Primer

<400> SEQUENCE: 52
aacacttgct agatcga                                                  17

<210> SEQ ID NO 53
<211> LENGTH: 18
<212> TYPE: DNA
<213> ORGANISM: Artificial Sequence
<220> FEATURE:
<223> OTHER INFORMATION: Probe

<400> SEQUENCE: 53
aaacacttgc tagatcaa                                                 18

<210> SEQ ID NO 54
<211> LENGTH: 22
<212> TYPE: DNA
<213> ORGANISM: Artificial Sequence
<220> FEATURE:
<223> OTHER INFORMATION: Probe

<400> SEQUENCE: 54
tgggtggagt agcgtctatc ag                                            22

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gaagcccttc ccctacatca                                               20

<210> SEQ ID NO 56
<211> LENGTH: 19
<212> TYPE: DNA
<213> ORGANISM: Artificial Sequence
<220> FEATURE:
<223> OTHER INFORMATION: Probe

<400> SEQUENCE: 56
cttcagtatt tggagtcca                                                19

<210> SEQ ID NO 57
<211> LENGTH: 23
<212> TYPE: DNA
<213> ORGANISM: Artificial Sequence
<220> FEATURE:
```

<223> OTHER INFORMATION: Probe

<400> SEQUENCE: 57
tcccttcccc atacgactta atg                        23

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
aatcttcagt attttgagtc c                          21

<210> SEQ ID NO 59
<211> LENGTH: 21
<212> TYPE: DNA
<213> ORGANISM: Artificial Sequence
<220> FEATURE:
<223> OTHER INFORMATION: Probe

<400> SEQUENCE: 59
ccattctgat tatagaaggc a                          21

<210> SEQ ID NO 60
<211> LENGTH: 22
<212> TYPE: DNA
<213> ORGANISM: Artificial Sequence
<220> FEATURE:
<223> OTHER INFORMATION: Probe

<400> SEQUENCE: 60
aagaagccct tccctacat ca                          22

<210> SEQ ID NO 61
<211> LENGTH: 20
<212> TYPE: DNA
<213> ORGANISM: Artificial Sequence
<220> FEATURE:
<223> OTHER INFORMATION: Probe

<400> SEQUENCE: 61
cattctgatt atggaaggca                            20

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
gggcacctga cacatgtaat ct                         22

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
ggttcctttc tcttgcggat aa                         22

```
<210> SEQ ID NO 64
<211> LENGTH: 17
<212> TYPE: DNA
<213> ORGANISM: Artificial Sequence
<220> FEATURE:
<223> OTHER INFORMATION: Probe

<400> SEQUENCE: 64
catcctctac tgcaaac                                                   17

<210> SEQ ID NO 65
<211> LENGTH: 21
<212> TYPE: DNA
<213> ORGANISM: Artificial Sequence
<220> FEATURE:
<223> OTHER INFORMATION: Primer

<400> SEQUENCE: 65
tgctgtcata agggacctac a                                              21

<210> SEQ ID NO 66
<211> LENGTH: 18
<212> TYPE: DNA
<213> ORGANISM: Artificial Sequence
<220> FEATURE:
<223> OTHER INFORMATION: Probe

<400> SEQUENCE: 66
atcctctacc gcaaactg                                                  18

<210> SEQ ID NO 67
<211> LENGTH: 18
<212> TYPE: DNA
<213> ORGANISM: Artificial Sequence
<220> FEATURE:
<223> OTHER INFORMATION: Probe

<400> SEQUENCE: 67
ttggactccg gtacatat                                                  18

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
aacaaccttg tctgatctgg aag                                            23

<210> SEQ ID NO 69
<211> LENGTH: 17
<212> TYPE: DNA
<213> ORGANISM: Artificial Sequence
<220> FEATURE:
<223> OTHER INFORMATION: Probe

<400> SEQUENCE: 69
actccggtgc atatttg                                                   17

<210> SEQ ID NO 70
<211> LENGTH: 23
<212> TYPE: DNA
<213> ORGANISM: Artificial Sequence
<220> FEATURE:
<223> OTHER INFORMATION: Primer
```

```
<400> SEQUENCE: 70
cacacaggag gagtgtagat acc                                              23

<210> SEQ ID NO 71
<211> LENGTH: 25
<212> TYPE: DNA
<213> ORGANISM: Artificial Sequence
<220> FEATURE:
<223> OTHER INFORMATION: Primer

<400> SEQUENCE: 71
tgacttggca ccattctatt ctaac                                            25

<210> SEQ ID NO 72
<211> LENGTH: 18
<212> TYPE: DNA
<213> ORGANISM: Artificial Sequence
<220> FEATURE:
<223> OTHER INFORMATION: Probe

<400> SEQUENCE: 72
cacccaagaa aattcaca                                                    18

<210> SEQ ID NO 73
<211> LENGTH: 18
<212> TYPE: DNA
<213> ORGANISM: Artificial Sequence
<220> FEATURE:
<223> OTHER INFORMATION: Probe

<400> SEQUENCE: 73
cacccaagaa cattcaca                                                    18

<210> SEQ ID NO 74
<211> LENGTH: 19
<212> TYPE: DNA
<213> ORGANISM: Artificial Sequence
<220> FEATURE:
<223> OTHER INFORMATION: Primer

<400> SEQUENCE: 74
cctcttcctc tgtcaggca                                                   19
```